(12) United States Patent
Inoue et al.

(10) Patent No.: US 8,211,450 B2
(45) Date of Patent: Jul. 3, 2012

(54) OPHTHALMIC COMPOSITION

(75) Inventors: Jun Inoue, Woodland Hills, CA (US); Tapan Shah, Woodland Hills, CA (US)

(73) Assignee: Senju USA, Inc., Woodland Hills, CA (US)

( * ) Notice: Subject to any disclaimer, the term of this patent is extended or adjusted under 35 U.S.C. 154(b) by 47 days.

(21) Appl. No.: 12/774,419

(22) Filed: May 5, 2010

(65) Prior Publication Data

US 2011/0275617 A1 Nov. 10, 2011

(51) Int. Cl.
*A61K 9/00* (2006.01)
(52) U.S. Cl. .................................................. 424/400
(58) Field of Classification Search .................... 424/400
See application file for complete search history.

(56) References Cited

U.S. PATENT DOCUMENTS

| | | | |
|---|---|---|---|
| 5,136,014 A * | 8/1992 | Figuly | 528/272 |
| 6,316,443 B1 * | 11/2001 | Baldwin | 514/226.5 |
| 6,432,423 B1 * | 8/2002 | Maignan et al. | 424/401 |
| 7,030,097 B1 | 4/2006 | Saltzman et al. | |
| 7,097,856 B2 | 8/2006 | Frechet et al. | |
| 7,109,247 B2 | 9/2006 | Baran, Jr. et al. | |
| 2001/0005717 A1 * | 6/2001 | Wagner et al. | 514/44 |
| 2005/0196617 A1 | 9/2005 | King | |
| 2006/0057215 A1 * | 3/2006 | Raiche et al. | 424/489 |
| 2006/0115531 A1 | 6/2006 | Chenault | |
| 2006/0204472 A1 * | 9/2006 | Paleos et al. | 424/78.27 |
| 2006/0257359 A1 | 11/2006 | Francois et al. | |
| 2007/0045596 A1 | 3/2007 | King et al. | |
| 2007/0048337 A1 | 3/2007 | Arthur | |
| 2008/0113027 A1 * | 5/2008 | Asgharian et al. | 424/484 |
| 2008/0180803 A1 | 7/2008 | Seybert et al. | |
| 2010/0008993 A1 | 1/2010 | Proksch et al. | |

FOREIGN PATENT DOCUMENTS

| | | |
|---|---|---|
| FR | 2 830 450 | 4/2003 |
| WO | 00/63409 | 10/2000 |
| WO | 01/66601 | 9/2001 |
| WO | 02/067908 | 9/2002 |
| WO | 02/074323 | 9/2002 |
| WO | 03/057270 | 7/2003 |
| WO | 03/089010 | 10/2003 |
| WO | 2004/060283 | 7/2004 |
| WO | 2004/087103 | 10/2004 |
| WO | 2006/031358 | 3/2006 |

(Continued)

OTHER PUBLICATIONS

Sigma-Aldrich, PAMAM dendrimer, ethylenediamine core, generation 3.0 solution, printed from http://www.sigmaaldrich.com/catalog/ProductDetail.do?D7=0&N5=SEARCH_CONCAT_PNO%7CBRAND_KEY&N4=412422%7CALDRICH&N25=0&QS=ON&F=SPEC on Sep. 24, 2010, 2 pages.*

(Continued)

*Primary Examiner* — Sreeni Padmanabhan
*Assistant Examiner* — Gigi Huang
(74) *Attorney, Agent, or Firm* — Wenderoth, Lind & Ponack, L.L.P.

(57) ABSTRACT

The present invention provides an ophthalmic composition comprising a hyperbranched polymer. The ophthalmic compositions may also comprise carbonic anhydrase inhibitors, wherein the hyperbranched polymer increases the aqueous solubility of the carbonic anhydrase inhibitor, and increases corneal permeation of the active agent. The ophthalmic compositions may also comprise non-ionic surfactants, such as polysorbate, hydroxypropyl methyl cellulose or hydroxyethyl cellulose, and beta-blockers, such as carteolol, levobunolol, betaxolol, metipranolol, timolol or propranolol.

11 Claims, 17 Drawing Sheets

FOREIGN PATENT DOCUMENTS

| WO | 2007/082331 | | 7/2007 |
|----|-------------|---|--------|
| WO | 2008/030591 | | 3/2008 |
| WO | WO 2008027340 | A2 * | 3/2008 |
| WO | 2008/054466 | | 5/2008 |
| WO | 2008/094722 | | 8/2008 |
| WO | 2009/064963 | | 5/2009 |
| WO | WO 2010017184 | A2 * | 2/2010 |

OTHER PUBLICATIONS

Merck & Co., Inc., Cosopt®, Jan. 2006, printed from http://web.archive.org/web/20060907112914/http://www.merck.com/product/usa/pi_circulars/c/cosopt/cosopt_pi.pdf on Sep. 24, 2010, 10 pages.*

Gupta et al.,Polypropylene Imine Dendrimer Mediated Solubility Enhancement: Effect of pH and Functional Groups of Hydrophobes, J Pharm Pharmaceut Sci, 10(3):358-367, 2007.*

Merck, Material Safety Data Sheet-Cosopt®, 2000, printed from http://wfldelearn.pssd.com/BinderView_PSS/vault/005/005436.pdf, 8 pages.*

Drugs.com, Brinzolamide (Ophthalmic), 1998, printed from http://www.drugs.com/mmx/brinzolamide.html?printable=1 on Sep. 24, 2010, 9 pages.*

Bochot, A., et al., "*Liposomes dispersed within a thermo sensitive gel: a new dosage form for ocular delivery of oligonucleotides*", Pharm.Res. 15, 1998, pp. 1364-1369.

Tejwani, R. W., et al., "*Study of Phase Behavior of Poly(ethylene glycol)- Polysorbate 80 and Poly(ethylene glycol)- Polysorbate 80-Water Mixtures*", J Pharmaceutical Sciences, 2000, vol. 89, pp. 946-950.

Vandamme, Th.F., and Brobeck, L., "*Poly(amidoamine) dendrimers as opthalmic vehicles for ocular delivery of pilocarpine nitrate and tropicamide*", J. Controlled Release, vol. 102, 2005, pp. 23-38.

Vandamme, Th.F., "*Microemulsions as ocular drug delivery systems: recent developments and future challenges*", Prog. Retin. Eye Res. 21, 2002, pp. 15-34.

Cheng, Y., et al., "*Dendrimers as drug carriers: Applications in different routes of drug administration*", J. Pharmaceutical Sciences, 2008, vol. 97, pp. 124-143.

Hassan, E., and Gallo, J.M., "*A simple rheological method for the in vitro asessment of mucin-polymer bioadhesive bond strength*", Pharmaceutical Research, vol. 7, 1990, pp. 491-495.

Sigurdsson, H.H., et al., "*Cyclodextrin formulation of dorzolamide and its distribution in the eye after topical administration*", J Controlled Release, 102, 2005, pp. 255-262.

Higashiyama, M., et al., "*Improvement of the ocular bioavailability of timolol by sorbic acid*", Int. J. of Pharmaceutics, 2004, vol. 272, pp. 91-98.

Rathore, M.S. and Majumdar, D.K., "*Effect of formulation factors on In vitro transcomeal permeation of gatifloxacin from aqueous drops*", AAPS PharmaSciTech 2006, 7, 3, Article 57.

Lester, M., "*Brinzolamide ophthalmic suspension: a review of its pharmacology and use in the treatment of open angle glaucoma and ocular hypertension*", Clinical Ophthalmol., Sep. 2008, 2(3), pp. 517-523.

Bravo-Osuna, I. and Herrero-Vanrell, R., "*Potential of Dendrimers as Drug Carriers in Ophthalmology*", Arch. Soc. ESP. Oftalmol., 2007, 82, pp. 69-70.

Banerjee, Pallab, et al., "*Novel hyper-branched Dendron for Gene Transfer in Vitro and in Vivo*", Bioconjugate Chem., 2004, pp. 960-968.

Kannan, Rangaramanujam, et al., "*Dendrimers and Hyperbranched Polymers for Drug Delivery*", Biomedical Applications of Nanotechnology, ed. Vinod Labhasetwar and Diadra L. Leslie-Pelecky, 2007, pp. 105-129.

Sahoo, Sanjeeb K. et al., "*Nanotechnology in ocular drug delivery*", Drug Discovery Today, vol. 13, Nos. 3/4, Feb. 2008, pp. 144-151.

Tomalia, D.A, et al., "*A New Class of Polymers: Starburst-Dendritic Macromolecules*", Polym. J., 17(1), 1985, pp. 117-132.

Hawker, C. and Frechet, J.M.J, "*A new convergent approach to monodisperse dendritic molecule*" J. Chern. Soc. Chern. Commun., 15, 1990, pp. 1010-1012.

Marano, R.J., et al., "*Dendrimer delivery of an anti-VEGF oligonucleotide into the eye: a long term study into inhibition of laser-induced CNV, distribution, uptake and toxicity*", Gene Therapy, 2005, 12(21), pp. 1544-1550.

Wathier, Michel, et al., "*Dendritic macromers as in situ polymerizing biomaterials for securing cataract incisions*", Journal of American Chemical Society, 2004, 126(40), pp. 12744-12745.

Grinstaff, Mark W., "*Dendritic polymers as ophthalmic sealants*", Abstracts of Papers, 228th ACS National Meeting, Philadelphia, PA, US, Aug. 22-26, 2004, PMSE-029.

Loutsch, Jeannette M., et al., "*Dendrimers: An innovative and enhanced ocular drug delivery system*", Drugs and Pharmaceutical Sciences, 2003, 130, Opthalmic Drug delivery Systems, 2nd Edition, pp. 467-492.

Seiler, Matthias, "Hyperbranched polymers: Phase Behavior and New Applications in the Field of Chemical Engineering", Fluid Phase Equilibria, 241 (2006), pp. 155-174.

Arce, Eva, et al. "Glycodendritic Structures Based on Boltorn Hyperbranched Polymers and Their Interactions with *Lens culinaris* Lectin", Bioconjugate Chem., 2003, 14, pp. 817-823.

P. Edman, "Biopharmaceuticals of Ocular Drug Delivery", CRC Press, Ann Arbor, 1993.

International Search Report and Written Opinion issued Jul. 25, 2011 in International (PCT) Application No. PCT/US11/35147, which claims priority to the present application.

B. Voit et al., "Hyperbranched and Highly Branched Polymer Architectures-Synthetic Strategies and Major Characterization Aspects", Chem. Rev., vol. 109, pp. 5924-5973, 2009.

D. Appelhans et al., "Hyperbranched PEI with Various Oligosaccharide Architectures: Synthesis, Characterization, ATP Complexation, and Cellular Uptake Properties", Biomacromolecules, vol. 10, pp. 1114-1124, 2009.

B. Cornils et al., Multiphase Homogeneous Catalysis, ISBN: 3-527-30721-4, pp. 1-24, 2005.

* cited by examiner

OPHTHALMIC COMPOSITION

FIELD OF THE INVENTION

The present invention relates to an ophthalmic composition comprising a hyperbranched polymer.

BACKGROUND OF THE INVENTION

Dorzolamide is a carbonic anhydrase inhibitor, and is one of the active ingredients in a topical drug for treating glaucoma (developed by Merck) called COSOPT®. The solubility of dorzolamide is 40 mg/mL at pH 4.0-5.5. It is a white to off-white, crystalline powder, which is soluble in water and slightly soluble in methanol and ethanol.

However, the COSOPT® formulation, which contains dorzolamide as the main active ingredient, is prepared at pH 5.65, due to the limited aqueous solubility of dorzolamide at physiological pH. Consequently, COSOPT® can lead to local irritation, due to the low pH. Dorzolamide has two pKa values of 6.35 and 8.5, which correspond to the protonized secondary amine group and the sulfonamide group, respectively. Dorzolamide is mainly in its hydrophilic cationic form at pH below 6.4, and in its hydrophilic anionic form above pH 8.5.

Thus, dorzolamide has a relatively low aqueous solubility in solutions with pH between 6.4 and 8.5, mainly because of dorzolamide's non-ionic behavior in that pH range.

AZOPT® (brinzolamide ophthalmic suspension) 1% is a sterile, aqueous suspension of brinzolamide, which has been formulated to be readily suspended and slow settling, following shaking. It has a pH of approximately 7.5 and an osmolality of 300 mOsm/kg. It is instilled for the reduction of elevated intraocular pressure in patients with open-angle glaucoma or ocular hypertension. Brinzolamide's pKa values are 5.9 (amine) and 8.4 (primary sulfonamide), allowing it to act as an acid or a base (ampholyte) depending upon the pH. It is mainly in its hydrophilic cationic form at pH below 5.9 and hydrophilic anionic form above pH 8.4. It is clear that brinzolamide is significantly less protonated (<10%) at physiological pH. Thus, brinzolamide has relatively low aqueous solubility in solutions with pH between 5.9 and 8.4, mainly because of brinzolamide is nonionic (lipophilic) behavior in that pH range.

Dendritic polymers are tree-like polymers that can be classified into two main types based on their branching architecture as "perfectly branched" (dendrimers) and "imperfectly branched" (hyperbranched polymers or HP). Hyperbranched polymers are molecular constructions having a branched structure, generally around a core. Unlike dendrimers, the structure of hyperbranched polymers generally lacks symmetry, as the base units or monomers used to construct the hyperbranched polymer can be of diverse nature and their distribution is non-uniform. The branches of the polymer can be of different natures and lengths. The number of base units, or monomers, may be different depending on the different branching. While at the same time being asymmetrical, hyperbranched polymers can have: an extremely branched structure, around a core; successive generations or layers of branching; a layer of end chains. Hyperbranched polymers are generally derived from the polycondensation of one or more monomers ABx, A and B being reactive groups capable of reacting together, x being an integer greater than or equal to 2. However, other preparation processes are also possible. Hyperbranched polymers are characterized by their degree of polymerization DP=1−b, b being the percentage of non-terminal functionalities in B which have not reacted with a group A. Since the condensation is not systematic, the degree of polymerization is less than 100%. An end group T can be reacted with the hyperbranched polymer to obtain a particular functionality on the ends of chains. See U.S. Pat. Nos. 6,432,423, 7,097,856, and U.S. Patent Publication 2006/0204472, the contents of which are incorporated herein by reference.

In contrast to the "structurally perfect" dendrimers prepared by multi-step synthesis, somewhat less perfect hyperbranched polymers can be synthesized in one-step reactions. Thus, unlike dendrimers, hyperbranched polymers are rapidly prepared with no purification steps needed for their preparation. Consequently, hyperbranched polymers are significantly less expensive than perfect dendrimers. Thus it makes HPs amenable for large-scale in vivo trials and bringing highly branched polymers as candidates for drug delivery of even common drugs as ibuprofen (Kannan, R. M. et al., *Biomedical Applications of Nanotechnology*, 2007, John Wiley & Sons Inc., p. 105).

OBJECT OF THE INVENTION

An object of the invention is to provide an improved ophthalmic composition, with improved aqueous solubility and corneal permeation of the active agent.

SUMMARY OF THE INVENTION

The present inventors have studied ophthalmic compositions comprising hyperbranched polymers. The present inventors have discovered that hyperbranched polymers are muco-adhesive polymers with a high force of bioadhesion, which provide strong electrostatic interactions between the negatively charged cornea mucin membrane and the cationic hyperbranched polymers.

The present inventors have also discovered that hyperbranched polymers increase the aqueous solubility of carbonic anhydrase inhibitors for glaucoma therapy, such as dorzolamide or brinzolamide. Additionally, the present inventors have discovered that the aqueous solubility of dorzolamide or brinzolamide increases linearly with an increase in the concentration of the hyperbranched polymer. Furthermore, the present inventors have discovered that hyperbranched polymers increase the corneal permeation and partitioning of dorzolamide and timolol into intact cornea, and increase the partitioning of dorzolamide and timolol (beta-blockers) into the lipophilic cornea membrane.

Accordingly, the present invention provides:

(1) An ophthalmic composition comprising a hyperbranched polymer.

(2) The ophthalmic composition according to the above (1), further comprising a carbonic anhydrase inhibitor.

(3) The ophthalmic composition according to the above (1) or (2), further comprising a non-ionic surfactant.

(4) The ophthalmic composition according to the above (1) or (2), wherein the weight average molecular weight of the hyperbranched polymer is in from 1,000 to 750,000 Daltons.

(5) The ophthalmic composition according to the above (1) or (2), wherein the hyperbranched polymer is selected from the group consisting of polyethylenimine, polypropylenimine and polyester.

(6) The ophthalmic composition according to the above (1), wherein the pH range is 5.0 to 8.0.

(7) The ophthalmic composition according to the above (1), wherein the concentration of the hyperbranched polymer is 0.001% to 5%.

(8) The ophthalmic composition according to the above (2), further comprising a beta-blocker.

(9) The ophthalmic composition according to the above (2), wherein the carbonic anhydrase inhibitor is selected from the group consisting of dorzolamide, brinzolamide and acetazolamide.

(10) The ophthalmic composition according to the above (3), wherein the non-ionic surfactant is selected from the group consisting of polysorbate 80, hydroxypropyl methylcellulose, and hydroxyethyl cellulose.

(11) The ophthalmic composition according to the above (8), wherein the beta-blocker is selected from the group consisting of carteolol, levobunolol, betaxolol, metipranolol, timolol and propranolol.

(12) An ophthalmic composition comprising a hyperbranched polymer, timolol, dorzolamide and polysorbate 80.

(13) An ophthalmic composition comprising a hyperbranched polymer, timolol, brinzolamide and polysorbate 80.

DETAILED DESCRIPTION OF THE INVENTION

Figure 1:
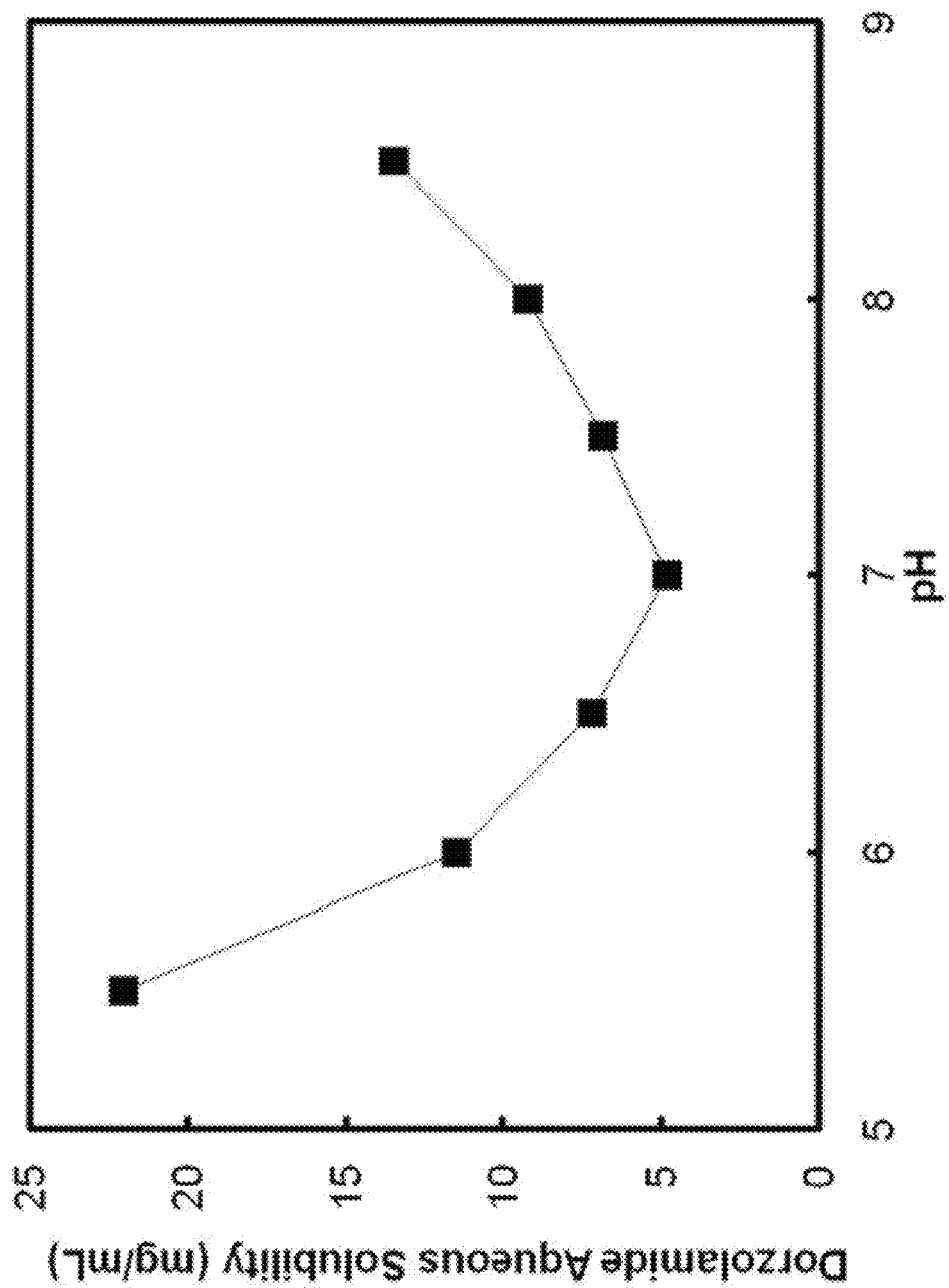
FIG. 1 shows the pH-solubility profile of dorzolamide in 0.1% (w/v) phosphate buffer.

The compositions of the present invention are topically administratable therapeutic compositions for treatment of conditions of the eye. Such conditions of the eye include glaucoma, and ocular diseases such as cataract, conjunctivitis, infection, inflammation or retinopathy.

A detailed description of the invention is provided below.

The present invention includes an ophthalmic composition comprising a hyperbranched polymer.

The hyperbranched polymer according to the present invention may be any hyperbranched polymer which is pharmaceutically acceptable, e.g., polyethylenimine, polypropylenenimine or polyester. The molecular weight of the hyperbranched polymer in the ophthalmic compositions of the present invention is in the range of from 1,000 to 750,000 Daltons. The molecular weight is weight average molecular weight measured by dynamic light scattering The concentration of the hyperbranched polymer in the ophthalmic compositions of the present invention is in the range of from 0.001% to 5%.

The ophthalmic composition discussed above may also comprise a carbonic anhydrase inhibitor. Carbonic anhydrase inhibitors are a class of pharmaceuticals that suppress the activity of carbonic anhydrase, and are known to be useful as anti-glaucoma agents. Examples of carbonic anhydrase inhibitors which may be present in the ophthalmic compositions of the present invention are dorzolamide, brinzolamide or acetazolamide.

The ophthalmic composition discussed above may also comprise a non-ionic surfactant. The non-ionic surfactant may be any non-ionic surfactant which is known as a pharmaceutically acceptable additive, for example, polysorbate 80, hydroxypropyl methylcellulose or hydroxyethyl cellulose.

The ophthalmic compositions of the present invention are advantageously used after being adjusted to a pH range which is conventionally adopted for topical application to the eye, and is normally employed after being adjusted to a pH of 3 to 8, preferably a pH of 5 to 8. For the pH adjustment, hydrochloric acid, acetic acid, sodium hydroxide, etc. can be used.

The ophthalmic compositions of the present invention may also comprise a beta-blocker. Beta-blockers are known to reduce the pressure within the eye (the intraocular pressure), and thus, are used to lessen the risk of damage to the optic nerve and loss of vision in patients with glaucoma. The beta-blocker in the ophthalmic compositions of the present invention may be any beta-blocker which is known as acceptable in ophthalmic compositions, such as carteolol, levobunolol, betaxolol, metipranolol, timolol and propranolol.

A specific embodiment of the present invention is an ophthalmic composition comprising a hyperbranched polymer, timolol, dorzolamide and polysorbate 80.

Such compositions preferably comprise about 0.001% to 5% of the hyperbranched polymer, most preferably about 0.01 to 0.1% (w/w), and 0.05 to 1% (w/w) of Timolol, most preferably about 0.5% (w/w), and about 0.05 to 5% (w/w) of dorzolamide, most preferably about 0.5 to 3% (w/w), and about 0.05 to 5% (w/w) of polysorbate 80, most preferably about 0.5 to 1% (w/w), and are to be administered once or twice a day to each affected eye.

A second specific embodiment of the present invention is an ophthalmic composition comprising a hyperbranched polymer, timolol, brinzolamide and polysorbate 80.

Such compositions preferably comprise about 0.001% to 5% of the hyperbranched polymer, most preferably about 0.01 to 0.1% (w/w), and 0.05 to 1% (w/w) of Timolol, most preferably about 0.5% (w/w), and about 0.05 to 5% (w/w) of brinzolamide, most preferably about 0.5 to 3% (w/w), and about 0.05 to 5% (w/w) of polysorbate 80, most preferably about 0.5 to 1% (w/w), and are to be administered once or twice a day to each affected eye.

The ophthalmic compositions according to the present invention may comprise a pharmacologically acceptable carrier, excipient or diluent which is known per se and may be formulated by a method known per se for preparing ophthalmic compositions. The ophthalmic compositions of the present invention may be provided in any pharmaceutical dosage form that is conventionally used as an ophthalmic preparation, e.g., eye drops and eye ointments.

The eye drop formulation may, for example, be an aqueous formulation, such as aqueous eye drops, aqueous suspension eye drops, viscous eye drops and solubilized eye drops, as well as non-aqueous formulations, such as non-aqueous eye drops and non-aqueous suspension eye drops.

The aqueous eye drop formulation may contain various additives incorporated ordinarily, such as buffering agents (e.g., phosphate buffers, borate buffers, citrate buffers, tartarate buffers, acetate buffers, amino acids, sodium acetate, sodium citrate and the like), isotonicities (e.g., saccharides such as sorbitol, glucose and mannitol, polyhydric alcohols such as glycerin, concentrated glycerin, polyethylene glycol and propylene glycol, salts such as sodium chloride), preservatives or antiseptics (e.g., benzalkonium chloride, benzethonium chloride, p-oxybenzoates such as methyl p-oxybenzoate or ethyl p-oxybenzoate, benzyl alcohol, phenethyl alcohol, sorbic acid or its salt, thimerosal, chlorobutanol and the like), solubilizing aids or stabilizing agents (e.g., cyclodextrins and their derivative, water-soluble polymers such as polyvinyl pyrrolidone, surfactants such as polysorbate 80 (Tween 80)), pH modifiers (e.g., hydrochloric acid, acetic acid, phosphoric acid, sodium hydroxide, potassium hydroxide, ammonium hydroxide and the like), thickening agents (e.g., hydroxyethyl cellulose, hydroxypropyl cellulose, methyl cellulose, hydroxypropylmethyl cellulose, carboxymethyl cellulose and their salts), chelating agents (e.g., sodium edetate, sodium citrate, condensed sodium phosphate) and the like.

The eye drop formulation in the form of an aqueous suspension may also contain suspending agents (e.g., polyvinyl pyrrolidone, glycerin monostearate) and dispersing agents (e.g., surfactants such as tyloxapol and polysorbate 80, ionic polymers such as sodium alginate) in addition to the additives listed above, whereby ensuring that the eye drop formulation is a further uniform microparticulate and satisfactorily dispersed aqueous suspension.

When the eye drop formulation in the form of an aqueous suspension is produced, it is preferable to use a pH modifier to make the formulation acidic pH (pH 4 to 5.5). A preferred pH modifier is hydrochloric acid.

The eye drop formulation in the form of an aqueous suspension preferably contains sodium citrate or sodium acetate as a buffering agent, concentrated glycerin and/or propylene glycol as an isotonicity and polyvinyl pyrrolidone as a suspending agent. A preferred dispersing agent is a surfactant and/or sodium alginate. Such surfactant is preferably tyloxapol or polysorbate 80.

The ophthalmic ointment may employ an ointment base known per se, such as purified lanolin, petrolatum, plastibase, liquid paraffin, polyethylene glycol and the like.

The ophthalmic composition of the present invention may be administered to a mammal which is or may be suffering from an ophthalmic disease, such as glaucoma (e.g., a human, rabbit, dog, cat, cattle, horse, monkey).

While the administration route and the dose may vary depending on a symptom, age and body weight of a subject, the concentration of the active agent in the ophthalmic composition of the present invention is about 0.001 to 5 (w/v) %, preferably about 0.01 to 3 (w/v) % contained in an aqueous eye drop formulation when given to an adult, and is given preferably 1 to 8 times a day with a single dose being one to several drops.

When given as the ophthalmic ointment, the dose is about 0.001 to 5 (w/v) %, preferably about 0.01 to 3 (w/v) %, and is given preferably 1 to 4 times a day as appropriate in view of the symptom.

Unless the intended purpose of use is affected adversely, the ophthalmic compositions of the present invention may contain or may be used together with other appropriate pharmacologically effective substances, for example, steroidal anti-inflammatory agents (dexamethasone, prednisolone and the like), non-steroidal anti-inflammatory agents (diclofenac sodium, pranoprofen and the like), antiallergic agents (tranilast, ketotifen fumarate, sodium cromoglicate and the like), antihistamic agents (diphenhydramine hydrochloride and the like), glaucoma-treating agents (pilocarpine hydrochloride, physostigmine salicylate, timolol, isopropylunoprostone and the like), antibiotics (gentamycin sulfate, fradiomycin sulfate, tobramycin, sulbenicillin, cefinenoxime, erythromycin, colistin, oxytetracycline, polymyxin B, chloramphenicol, micronomicin, dibekacin, sisomicin and the like), antibacterial agents (sulfamethizole, sulfamethoxazole, ofloxacin, norfloxacin, lomefloxacin hydrochloride, enoxacin, ciprofloxacin hydrochloride, cinoxacin, sparfloxacin, tosufloxacin tosylate, nalidixic acid, pipemidic acid trihydrate, pipemidic acid, fleroxacin, levofloxacin and the like), and antiviral agents (idoxuridine, acyclovir and the like), and antimycotic agents (pimaricin, fluconazole, miconazole, amphotericin B, flucytosine, itraconazole and the like).

The ophthalmic compositions of the present invention may be produced by dissolving or dispersing the active agent(s), hyperbranched polymer and optionally the non-ionic surfactant in a solution appropriately containing pharmaceutically acceptable additives, such as isotonicity agents, buffers, preservatives, suspending agents, thickeners, stabilizers, pH adjusting agents, and the like.

The present invention is further illustrated in detail by the following Experimental Examples. These Experimental Examples are merely illustrative, and are not intended to limit the scope of the present invention.

EXPERIMENTAL EXAMPLE 1 pH-solubility profile of dorzolamide in aqueous solution containing different concentrations of hyperbranched polymers (Lupasol® G20, Lupasol® G 35, Lupasol® PS) and polyethylene glycol.

Methods

Suspensions of dorzolamide hydrochloride in 0.1% phosphate buffer solution at pH 5.5, pH 6, pH 6.5, pH 7, pH 7, pH 8 and pH 8.5 were prepared. Similar suspensions were also prepared in aqueous solution containing different concentrations of different HPs and polyethylene glycol (PEG) with a molecular weight of 8000. A combination of polysorbate 80 and PEG 8000 was also attempted. The pH was measured accurately with micro-pH electrode (Thermo Scientific). The desired pH was adjusted using either 1 M NaOH or 1 M HCl. The suspension solutions were first stirred for 10 min at room temperature (with heating up to 60° C. for 5 minutes). After allowing the suspensions to equilibrate at room temperature for an additional 30 minutes, the suspension solutions were then sonicated for 10 minutes and finally filtered through 0.45 μm syringe filters. The filtrates were analyzed for dorzolamide concentration using UPLC. The dorzolamide detection was performed using: a gradient 1% Triethylamine (TEA) in water:acetonitrile method, performed at room temperature, with the flowrate of 0.7 mL/min, at 254 nm wavelength and 10 µL injection volume, on BEH C18 1.7 µm, 2.1×50 mm column. A calibration curve was prepared to find the dorzolamide concentration. The properties of polymers used are listed in Table 1.

TABLE 1

Properties of HPs in EXPERIMENTAL EXAMPLE 1.

| Polymer name | Viscosity (cP) | Molecular weight | pKa | Solid content |
|---|---|---|---|---|
| Lupasol ® G 20 | 200-500 | 1300 | 7-10 | >98% |
| Lupasol ® G 35 | 250-650 | 2000 | 7-10 | 48-52% |
| Lupasol ® PS | 1000-2500 | 750,000 | 7-10 | 33% |

Results and Discussion

Figure 2:
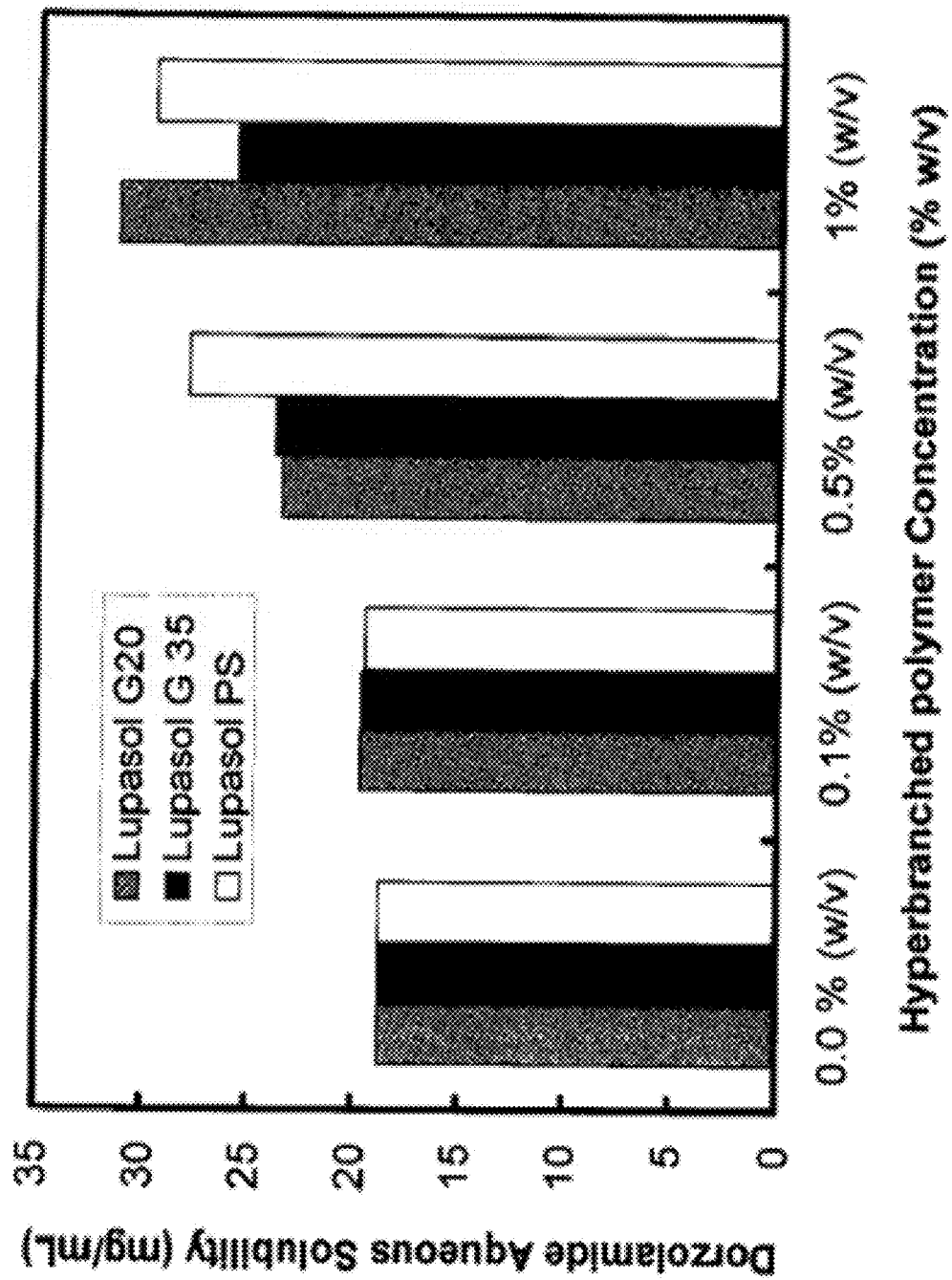
FIG. 2 shows the dependence of hyperbranched polymer concentration on the aqueous solubility of dorzolamide in 0.1% (w/v) phosphate buffer at pH 5.65.
Figure 3:
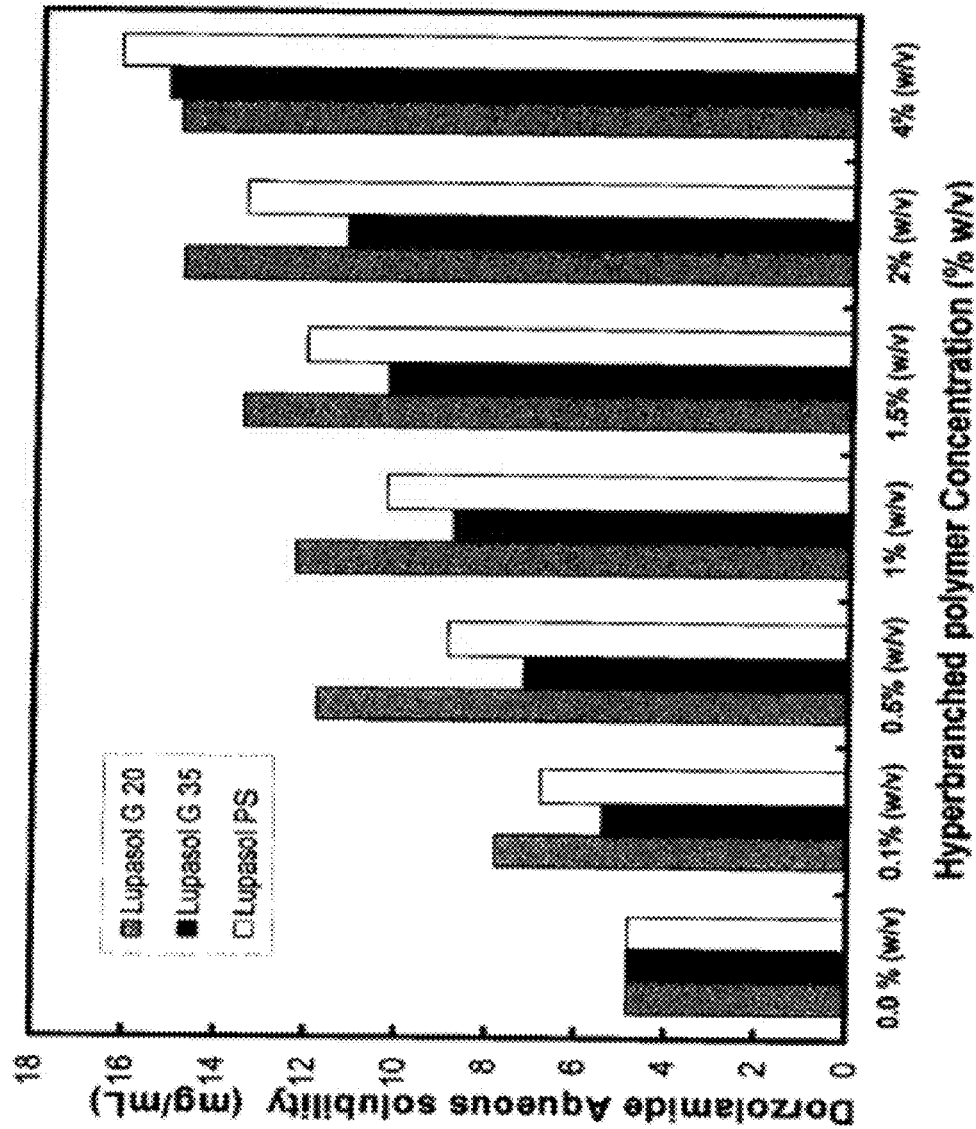
FIG. 3 shows the dependence of hyperbranched polymer concentration on the aqueous solubility of dorzolamide in 0.1% (w/v) phosphate buffer at pH 7.

FIG. 1 demonstrates that the aqueous solubility of dorzolamide decreases as the pH increases from 5.65, and reaches a bottom at pH 7. Since COSOPT® is formulated at pH 5.65, dorzolamide solubility in 0.1% (w/v) phosphate buffer was quantified in the presence of different HPs of different concentrations at pH 5.65. The result is presented in FIG. 2. The solubility of dorzolamide increased at pH 5.65 with the increase in concentrations of HPs from 0.1% to 1%. Similarly at pH 7, as shown in the bar graph of FIG. 3, the dorzolamide solubility increased linearly with the increase in concentration of HPs from 0.1% (w/v) to 4% (w/v).

Figure 4:
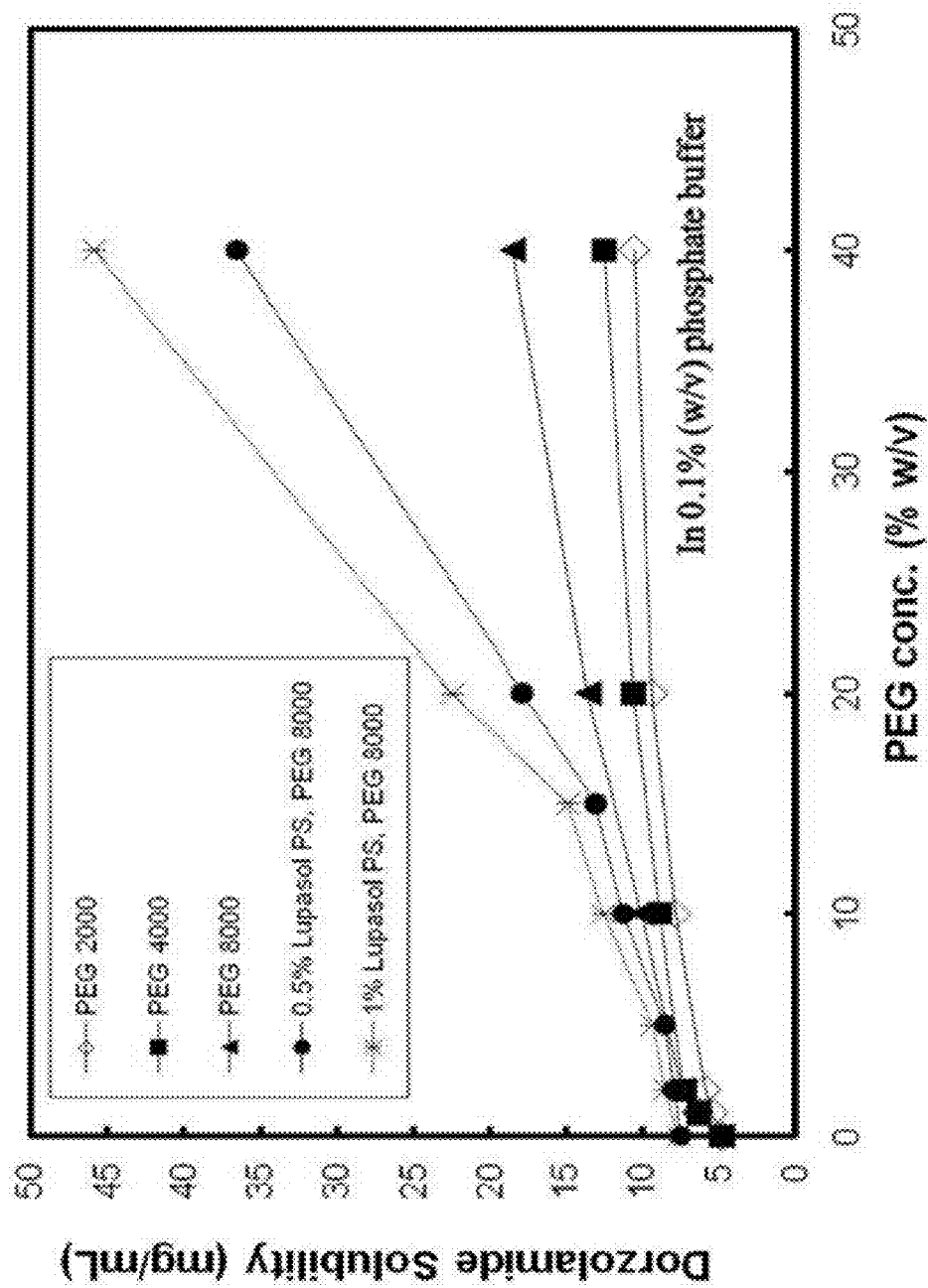
FIG. 4 shows the effect of a combination of PEG 8000 and hyperbranched polymer (Lupasol® PS) with various concentrations on the aqueous solubility of dorzolamide at pH 7.

As shown in FIG. 4, combinations of various concentrations of PEG 8000 and 0.5% and 1% (w/v) of hyperbranched polymer (Lupasol® PS) were applied at pH 7. It is clear from FIG. 4 that 2% (w/v) solubility of dorzolamide (similar to COSOPT®) in phosphate buffer at pH 7 can be achieved by using about 20% PEG 8000 and 0.5% of Lupasol® PS, or 17% of PEG 8000 and 1% Lupasol® PS.

Conclusion

The present inventors discovered that the aqueous solubility of dorzolamide increased with an increase in the concentration of HP and PEG. In the case of PEG, the solubility also increased linearly with an increase in the molecular weight of the PEG. The aqueous solubility of dorzolamide increased dramatically with the addition of 2% PEG 8000 and 1% polysorbate 80 in phosphate buffer (0.1%, pH 7). Further, the polysorbate 80 assists in dispersing the dorzolamide molecules and inhibits the precipitation in water in presence of PEG.

From these results, it is concluded that HP significantly enhances the solubility of hydrophobic dorzolamide. Additionally, hydrophilic polyethylene glycol was discovered to be a dorzolamide solubility enhancer. Furthermore, a combination of low concentrations of polysorbate 80 and PEG 4000 also proved to be useful additives for enhancing the solubility of hydrophobic dorzolamide.

The results demonstrate the advantages of using hyperbranched polymers and PEG as hydrophobic dorzolamide solubility enhancing additives at pH values closer to physiological pH that are more conducive for penetration of dorzolamide through the cornea membrane. In addition, these polymers may provide bio-adhesive properties necessary for increasing the ocular residence time of dorzolamide on the eye surface. Polysorbate also proved to be an effective emulsifier, suppressing the precipitation of poorly soluble dorzolamide at pH 7, in the presence of PEG.

EXPERIMENTAL EXAMPLE 2

A simple rheological method for the in vitro assessment of mucin-hyperbranched polymer bioadhesive bond strength.

A simple viscometric method was adopted to quantify the mucin-polymer bioadhesive bond strength. In order to determine the muco-adhesive properties of commercially available hyperbranched polymers (HP) called polyethyleneimine, the force of bioadhesion was calculated for different concentrations of HPs with porcine gastric mucin at pH 7 in comparison with the market product COSOPT®. Porcine gastric mucin was used as a model mucin. However, since all mucins appear to share general physical, structural, and rheological properties, it is believed that porcine gastric mucin is a satisfactory model for primary evaluation of bioadhesive materials.

The viscosities of low concentrations of HPs, 15% (w/v) mucin, and COSOPT® were also compared at different shear rates. The viscosity of low concentration (0.5% and 1%) HP solution in phosphate buffer was observed to be close to that of water at high shear rates (80 s$^{-1}$). The viscosities of these solutions containing hyperbranched polymer were significantly lower than COSOPT®, suggesting the suitability of HPs with topical ophthalmic formulations.

The bioadhesive properties of HP evaluated in terms of force of bioadhesion revealed the muco-adhesive behavior of HP. The force of bioadhesion of 1% HP-mucin was more than two times of COSOPT®-mucin at shear rate of 80 s$^{-1}$.

Overall, the proven bioadhesive properties of HPs could be very helpful increasing the residence time of the active ingredients on the cornea for topical ophthalmic applications.

The term bioadhesion describes a phenomenon in which synthetic or biological macromolecules and hydrocolloids are able to adhere to a biological tissue, and the force of bioadhesion is the interfacial force which holds together the adhesive material and the biological tissue. Polymer-mucin bioadhesion may improve the residence time of the preparation in the conjunctivae sac. A sustained effect is expected when the polymer is capable of binding to the mucus layer coating the corneal and conjunctivae epithelium. The polymer-mucin interactions may include chain interlocking, conformation changes and non-covalent bond formation. A higher force of bioadhesion, determined by viscosity measurement, indicates a prolonged contact time at the corneal application site.

The force of bioadhesion (F) was calculated as per the following equation (1):

$$F = \eta_b \sigma \qquad (1),$$

where $\sigma$ is the rate of shear per second, and $\eta_b$ is based on experimental measured values as per the following equation (2):

$$\eta_b = \eta_t - \eta_m - \eta_p \qquad (2),$$

where $\eta_t$ is the viscosity coefficient of the system, and $\eta_m$ and $\eta_p$ are the individual viscosity coefficients of mucin and the bioadhesive polymer (e.g., hyperbranched polymer and PEG 8000), respectively.

For equations (1) and (2) to be valid, $\eta_t$, $\eta_m$ and $\eta_p$ should be measured at the same concentration, temperature, time, and rate of shear. The bioadhesive phenomenon plays a dominant role in the contact time of aqueous tear that substitute in the precorneal area.

Methods

Brookfield Rotational L VDVE viscometer was employed for all measurements. Spindle with code number 18 was used for all viscosity measurements. A factor of 1.32 was used to convert rpm to shear rate ($s^{-1}$) as per the manual. A solution of 15% of gastric mucin was prepared in 0.1% (w/v) phosphate buffer at pH 7. The individual viscosities 0.5% and 1% of hyperbranched Lupasol® PS in phosphate buffer solution were measured. The viscosities of 15% mucin in phosphate buffer were also measured. The viscosity was measured at 20° C. at different shear rates D from 2.6 to 80 $s^{-1}$. (Hassan, E. et al., *Pharm Res.* 5 (1990) 491) Five samples of 10 mL each were prepared with different concentrations of Lupasol® PS, PEG and with and without 15% gastric mucin in 0.1% phosphate buffer at pH 7.

TABLE 2

Contents (%) of Test Samples

| Content | #1 | #2 | #3 | #4 | #5 | #6 |
|---|---|---|---|---|---|---|
| Lupasol ® PS | — | 0.5 | 0.5 | 1 | 1 | 1 |
| Gastric mucin | 15 | — | 15 | — | 15 | 15 |
| PEG 8000 | — | — | — | — | — | 2 |
| 1M NaOH | Adjust pH to 7.0 | Adjust pH to 7.0 | Adjust pH to 7.0 | Adjust pH to 7.0 | Adjust pH to 7.0 | Adjust pH to 7.0 |

Sample #7 is the original COSOPT® market product. The viscosity at 20° C. was measured at different shear rates. The force of bioadhesion was calculated using equations (1) and (2), discussed above.

Results & Discussion

Figure 5:
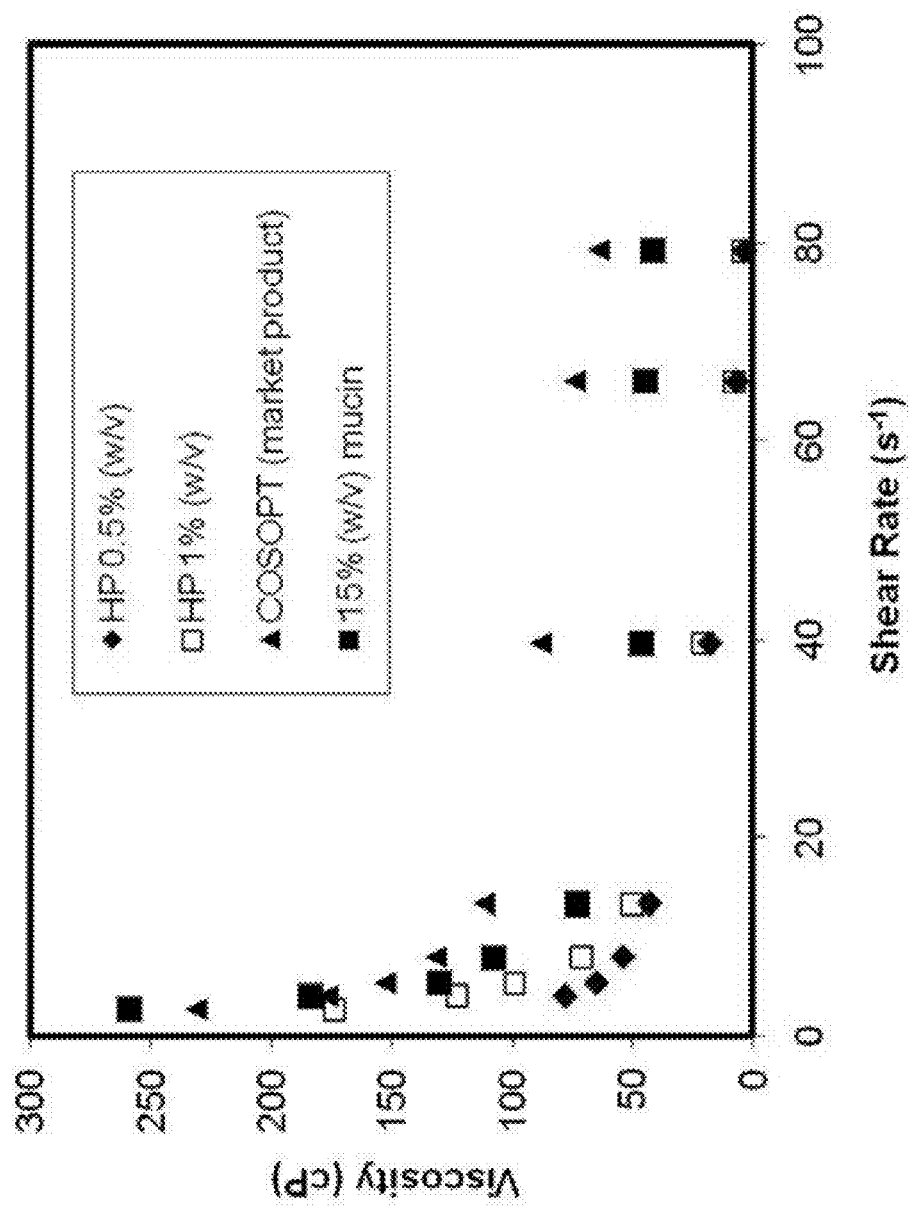
FIG. 5 shows the viscosity as a function of shear rate at 20° C. of different solutions in 0.1% (w/v) phosphate buffer.

As shown in FIG. 5, the low concentrations of HPs in phosphate buffer have relatively less viscosity compared to COSOPT® (Sample #7) and mucin (Sample #1). The viscosities of HP (0.5%, Sample #2 and 1%, Sample #4) are relatively close to water at high shear rates. In addition, at high shear rates the difference between the viscosities of 0.5% HP and 1% are negligible. The result clearly suggests the advantage of using HP as an additive with rheological properties, that may be very compatible for topical ophthalmic solutions since the addition of HP to a formulation may not change the rheological properties of final formulation.

The force of bioadhesion was quantified based on the data available from FIG. 5 at shear rate of 80 $s^{-1}$. High shear rate was chosen since the polymers typically exhibit bioadhesive properties at high shear rates (close to 100 $s^{-1}$).

Figure 6:
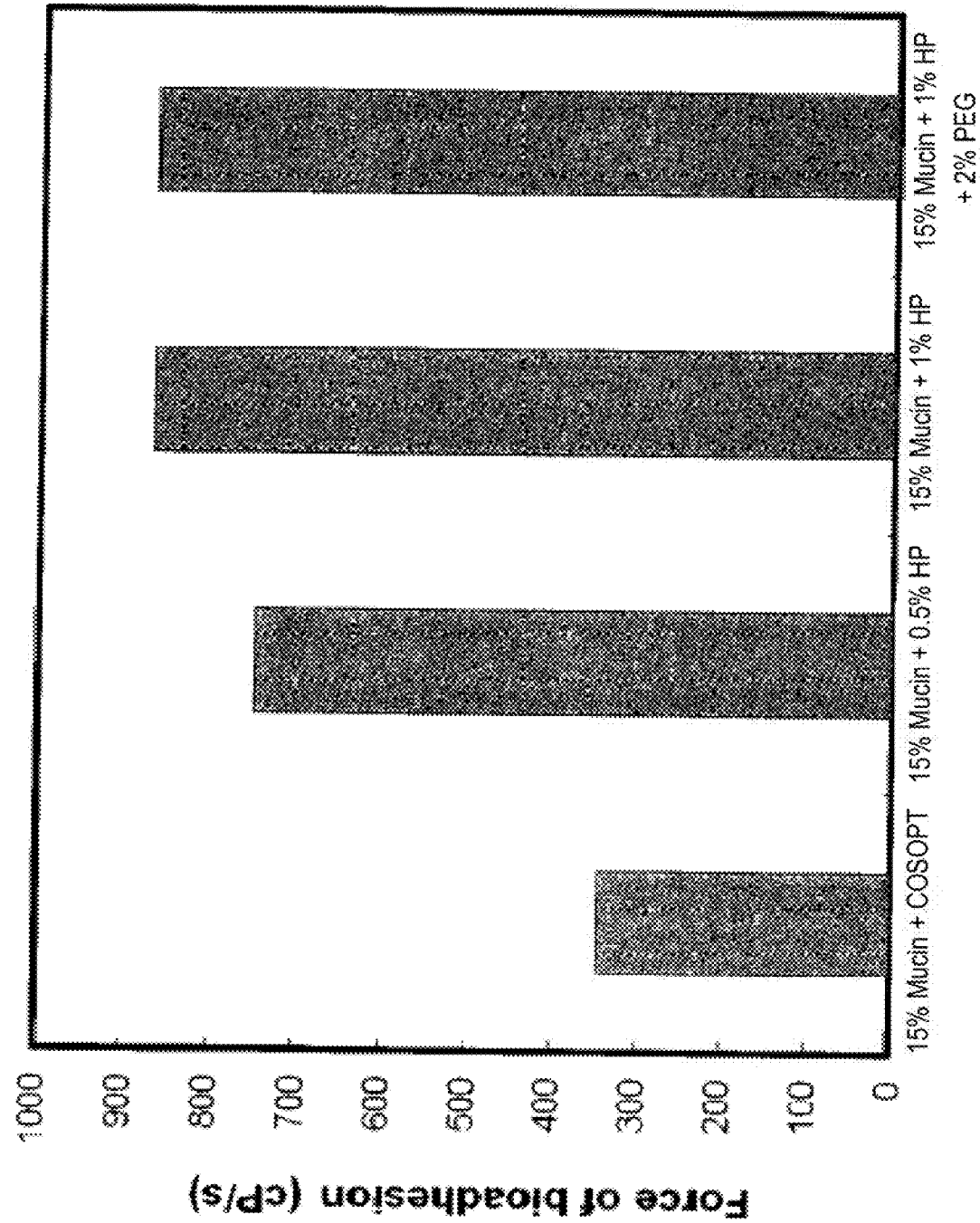
FIG. 6 shows the force of bioadhesion at pH 7 and shear rate of 80 $s^{-1}$.

As shown in FIG. 6, the bioadhesive bond strength of low concentrations (0.5% and 1%) of HP-mucin system is almost more than two times to that of COSOPT®-mucin system. The addition of 2% PEG did not change the force of bioadhesion of 1% HP-mucin system, suggesting that 2% PEG may not have influence on force of bioadhesion caused by the HP at pH 7. Overall, the results shown in FIG. 6 indicate that the bioadhesive strengths of low concentrations of HPs are relatively significant compared to the polymers present in COSOPT® formulation. The bioadhesive phenomenon may be very conducive for increasing the ocular bioavailability of the drug.

Conclusion

In conclusion, data generated by the viscometric assessment method of bioadhesion suggests that the hyperbranched polymers are bio-adhesive additive materials that could strongly interact with ocular mucin. These bioadhesive forces between mucin and HP could eventually lead to enhancement of the ocular bioavailability of the drug.

EXPERIMENTAL EXAMPLE 3

Aqueous solubility of dorzolamide in the presence of timolol for a novel formulation containing hyperbranched polymer (HP) and polysorbate 80 or a combination of polyethylene glycol (PEG) and polysorbate 80 at pH 5.65 and pH 7.

Methods

A suspension of dorzolamide hydrochloride and 0.7% timolol in citrate buffer solution at pH 5.65 was prepared (Control sample). A similar suspension was also prepared in aqueous solution containing 2% of hyperbranched polymer (Lupasol® PS) in citrate buffer of pH 3. The final pH was adjusted to 5.65 with 1 M NaOH after addition of HP (sample 1). The combination of different molecular weight PEG and polysorbate 80 at pH 5.65 as per Table 3 were also attempted. Table 3 shows all the different test samples suspensions to be prepared in 10 mM citrate buffer.

TABLE 3

Different Test formulations prepared at pH 5.65 in citrate buffer, and at pH 7 in phosphate buffer.

| Content | Control Sample | S #1 | S #2 | S #3 | S #4 | S #5 | S #6 | S #7 | S #8 |
|---|---|---|---|---|---|---|---|---|---|
| Dorzolamide HCl | >2.22 | >2.22 | >2.22 | >2.22 | >2.22 | >2.22 | >2.22 | >2.22 | >2.22 |
| Timolol Maleate | 0.683 | 0.683 | 0.683 | 0.683 | 0.683 | 0.683 | 0.683 | 0.683 | 0.683 |
| Lupasol ® PS (MW = 750k) | — | 2% (w/v) | — | — | — | — | — | — | — |
| PEG 200 | — | — | 2 | — | — | — | — | — | — |

TABLE 3-continued

Different Test formulations prepared at pH 5.65 in citrate buffer, and at pH 7 in phosphate buffer.

| Content | Control Sample | S #1 | S #2 | S #3 | S #4 | S #5 | S #6 | S #7 | S #8 |
|---|---|---|---|---|---|---|---|---|---|
| PEG 400 | — | — | — | 2 | — | — | — | — | — |
| PEG 2000 | — | — | — | — | 2 | — | — | — | — |
| PEG 3350 | — | — | — | — | — | 2 | — | — | — |
| PEG 4000 | — | — | — | — | — | — | 2 | — | — |
| PEG 8000 | — | — | — | — | — | — | — | 2 | — |
| PEG 20000 | — | — | — | — | — | — | — | — | 2 |
| Polysorbate 80 | — | — | 1 | 1 | 1 | 1 | 1 | 1 | 1 |
| In 10 mM citrate or phosphate buffer | Adjust pH to 5.65/7 | Adjust pH to 5.65/7 | Adjust pH to 5.65/7 | Adjust pH to 5.65/7 | Adjust pH to 5.65/7 | Adjust pH to 5.65/7 | Adjust pH to 5.65/7 | Adjust pH to 5.65/7 | Adjust pH to 5.65/7 |

Similarly, the formulations were again prepared in 10 mM phosphate buffer (Table 3) for the formulations to be tested for dorzolamide solubility at pH 7 in phosphate buffer rather than citrate buffer. The suspension solutions were first stirred for 10 min at room temperature (with heating up to 60° C. for 5 minutes). After allowing the suspensions to equilibrate at room temperature for an additional 30 minutes, the suspension solutions were then sonicated for 10 minutes and finally filtered through 0.45 μm syringe filters. The filtrates were analyzed for dorzolamide and timolol concentration using UPLC. The conditions for dorzolamide and timolol maleate detection were: a gradient 1% Triethylamine (TEA) in water: acetonitrile method, performed at room temperature, with the flow rate of 0.7 mL/min, at 254 nm and 298 nm wavelength and 1 μL injection volume, on BEH C18 1.7 urn, 2.1×50 mm column. A calibration curve was prepared to find the dorzolamide concentration.

Results and Discussion

Figure 7:
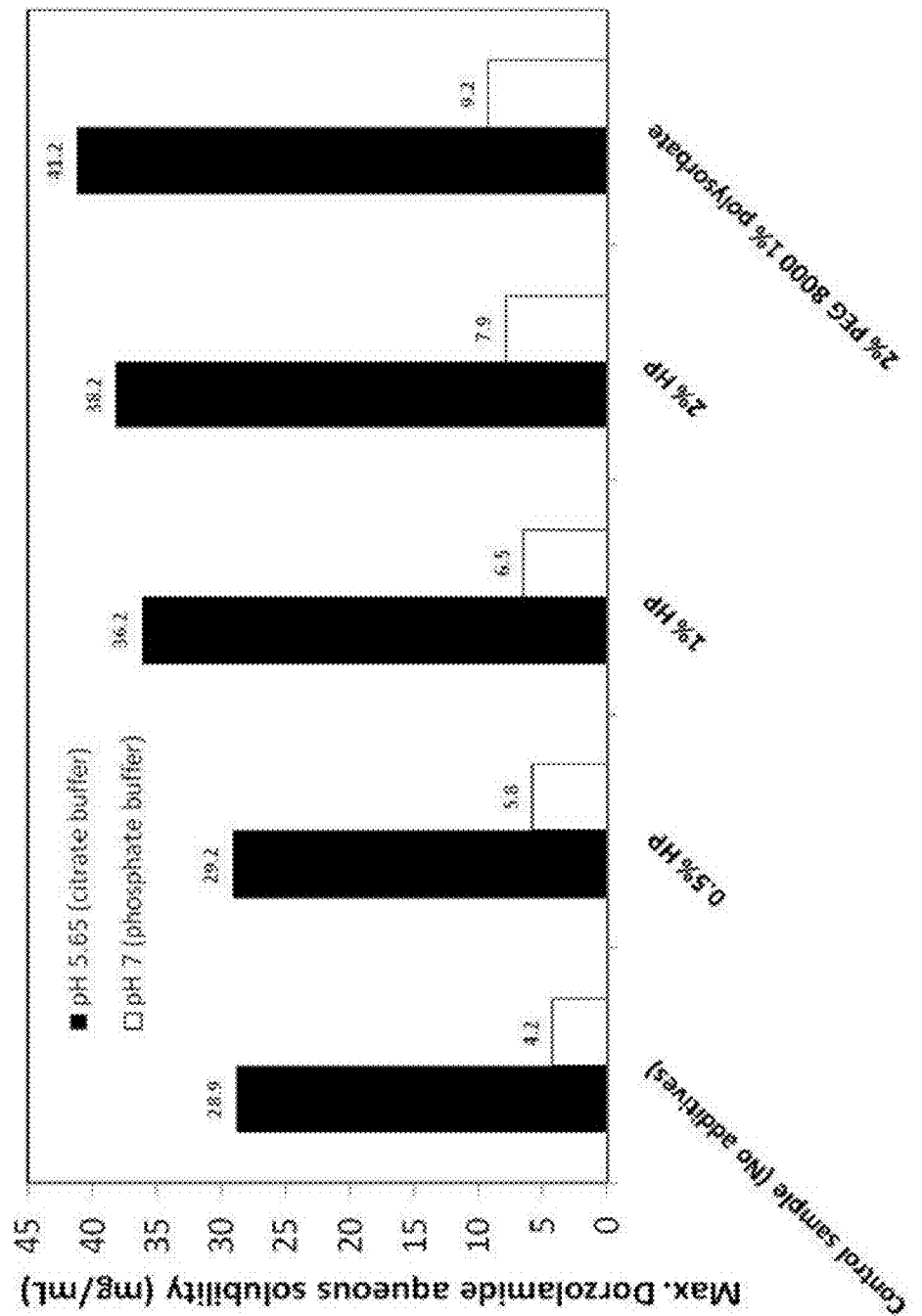
FIG. 7 shows the maximum aqueous solubility of dorzolamide at pH 5.65 and pH 7 with addition of additives in the presence of 0.5% timolol in the aqueous solution in all cases.

In this experiment, the present inventors used hyperbranched polymers, PEG, and polysorbate 80 as solubility enhancer additives. Different combinations were attempted at pH 5.65 and pH 7. As shown in FIG. 7, the solubility of dorzolamide was shown to increase with the addition of additives, compared to the control sample without additives, at pH 5.65 and pH 7 in the presence of timolol. At pH 5.65, in all cases the solubility of dorzolamide was above 2%, and therefore the addition of HP or PEG and polysorbate 80 combination increased solubility of dorzolamide in the presence of timolol.

Figure 8:
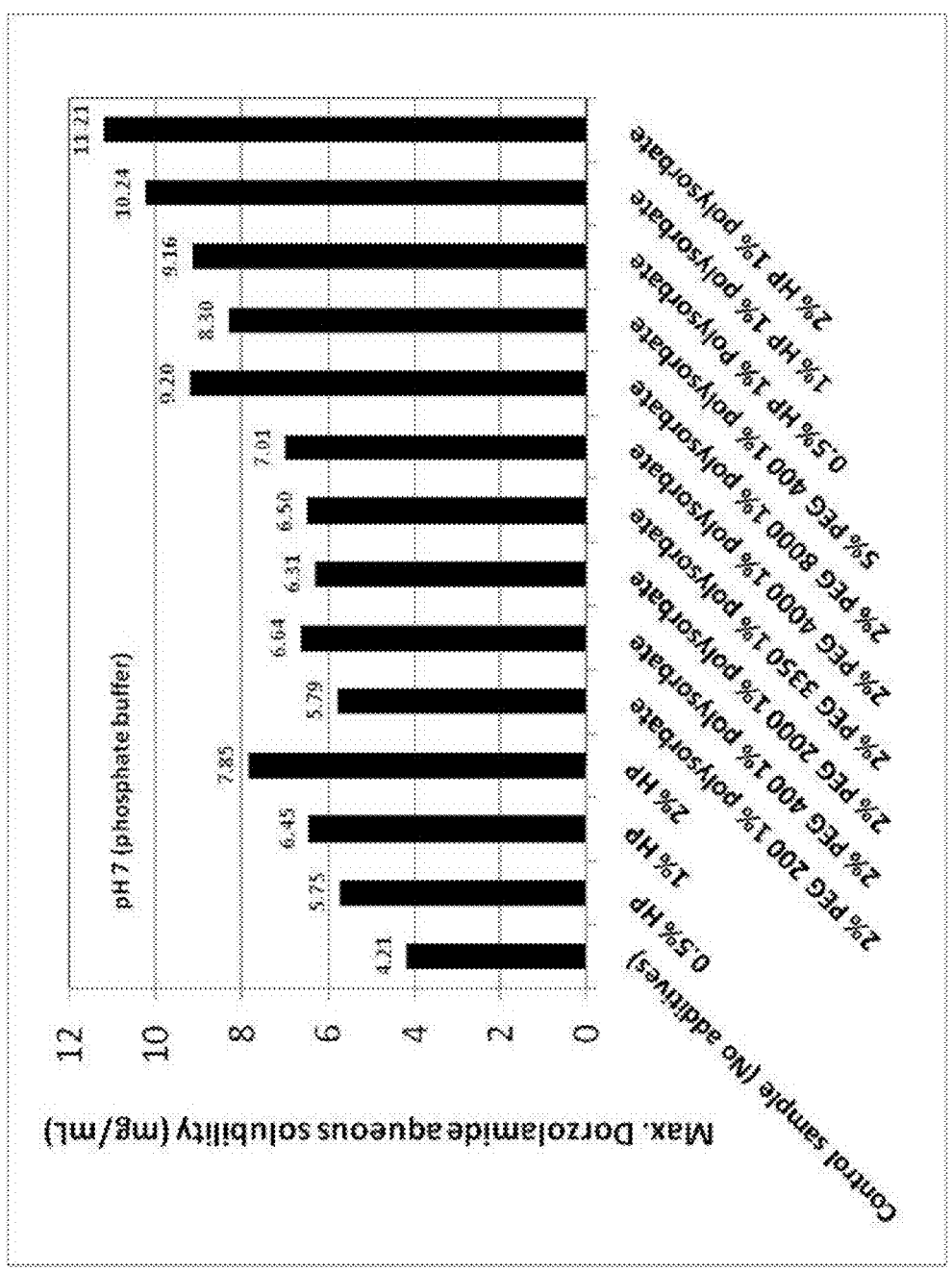
FIG. 8 shows the maximum dorzolamide solubility at pH 7 with different combinations of additives in the presence of 0.5% timolol.

While the market COSOPT® product has 2% dorzolamide at pH 5.65, the enhancement of solubility at pH 5.65 with more than 2% dorzolamide solubility by addition of HP or PEG will not have useful contribution to efficacy enhancement of drug by increasing the dosage. Thus, the solubility data at pH 7 is more vital, where dorzolamide has poor solubility (less than 0.5% w/v solubility) in 10 mM phosphate buffer. It was also noted that the solubility of timolol in the formulation samples (each containing exactly 0.5% w/v timolol) did not change at pH 5.65 and pH 7 with the addition of additives. Since COSOPT® is formulated at pH 5.65, the dorzolamide solubility in the presence of timolol was quantified by the addition of different hyperbranched polymers of different concentrations at pH 5.65 to the formulation sample. The result is presented in FIG. 7. As shown in the bar graph, the dorzolamide solubility increases linearly with the increases in concentration of hyperbranched polymers from 0.5% to 2% at pH 5.65 and pH 7. However, the impact of HP to solubility enhancement of dorzolamide is more pronounced at pH 5.65 than pH 7. As shown in FIG. 8, the addition of polysorbate 80 to HP increase the dorzolamide solubility.

The improvement in aqueous solubility of dorzolamide in the presence of timolol was significant with the additions of a hyperbranched polymer or a combination of PEG and polysorbate 80 at pH 5.65. In this case, the polysorbate 80 helped in dispersing the dorzolamide molecules and inhibited the precipitation in water in the presence of PEG. A combination of hyperbranched polymer and polysorbate 80 was the best combination for enhancement of dorzolamide solubility in presence of timolol at pH 7. From the results, it can be concluded that hyperbranched polymer and polysorbate 80 significantly enhance the solubility of hydrophobic dorzolamide in the presence of timolol at pH 7. Hydrophilic polyethylene glycol also turned out to be a dorzolamide solubility enhancer. Furthermore, a combination of low concentrations of polysorbate 80 and PEG 8000 also proved to be a very useful additive for enhancement of solubility of hydrophobic dorzolamide. Overall, a formulation at pH 7 with optimized concentration of hyperbranched polymer (Lupasol® PS) and polysorbate could be very useful for increasing the ocular bioavailability.

Conclusion

The results clearly indicate the advantages of using hyperbranched polymers and polysorbate 80 as hydrophobic dorzolamide solubility enhancing additives at pH values closer to physiological pH that are more conducive for penetration of close to 1% dorzolamide through cornea membrane. In addition, these polymers may provide bioadhesive properties necessary for increasing the ocular residence time of dorzolamide on eye surface. Polysorbate 80 also proved to be an effective emulsifier, suppressing the precipitation of poorly soluble dorzolamide at pH 7 in the presence of a hyperbranched polymer.

EXPERIMENTAL EXAMPLE 4

In vitro corneal permeation study of dorzolamide and timolol for novel topical formulations containing hyperbranched polymer and Polysorbate 80.

In vitro experiments on the corneal permeation of dorzolamide and timolol (active ingredients of COSOPT®) were carried out to investigate the effect of the addition of 0.5% polyethyleneimine hyperbranched polymer (HP), or the addition of 0.5% HP and 1% polysorbate 80, in comparison to the original market topical formulation (only active ingredients) at pH 5.65. This experiment reports the data for in vitro transcorneal permeation of dorzolamide and timolol from a novel formulation containing a hyperbranched polymer (polyethyleneimine) and polysorbate 80, compared to COS-OPT® formulation with only active ingredients (control sample) at pH 5.65.

Materials and Methods

Experimental Method
1. Formulation Preparation: The following three solutions in 10 mM citrate buffer were formulated for examining the in vitro corneal permeation of dorzolamide and timolol, as well as determining the corneal hydrolysis effect.

| Content | Composition (% w/v) | | |
|---|---|---|---|
| | Test sample 1 (n = 2) | Test sample 2 (n = 2) | Test sample 3 (n = 2) |
| Dorzolamide | 2 | 2 | 2 |
| Timolol | 0.5 | 0.5 | 0.5 |
| HP | — | 0.5 | 0.5 |
| Polysorbate 80 | — | — | 1 |
| 1M NaOH | Adjust pH to 5.65 | Adjust pH to 5.65 | Adjust pH to 5.65 |

The samples were filtered by 0.45 μm filter syringe. The initial concentration of both the samples was determined by UPLC analysis. From the experimental data, the following inferences were made:
 a) Hyperbranched polymer significance exclusively (from Test 1 and Test 2 data comparison).
 b) Polysorbate 80 (Test 2 & Test 3 comparison) significance on cornea permeation.
 c) Hyperbranched polymer+polysorbate 80 combination significance (from Test 1, Test 2, Test 3 data comparison).
The samples were filtered by 0.45 μm filter syringe to remove the precipitates, if any. The initial concentration of all the samples was determined by UPLC analysis.
2. In Vitro Rabbit Corneal Permeation Experiment

TABLE 4

Composition of receptor solution for in vitro cornea permeation experiment.

| Composition | Chemical Formula | [g/100 mL] |
|---|---|---|
| Calcium chloride | $CaCl_2$ | 0.0132 |
| Potassium chloride | KCl | 0.04 |
| Magnesium sulfate | $MgSO_4 \cdot 7H_2O$ | 0.02 |
| Sodium dihydrogen phosphate dehydrate | $NaH_2PO_4 \cdot 2H_2O$ | 0.0187 |
| Sodium chloride | NaCl | 0.787 |
| Glucose | Glucose | 0.1 |
| Sodium hydroxide | NaOH | q.s. |
| Water | Purified Water | q.s |
| pH | pH | 7.2 |

Figure 9:
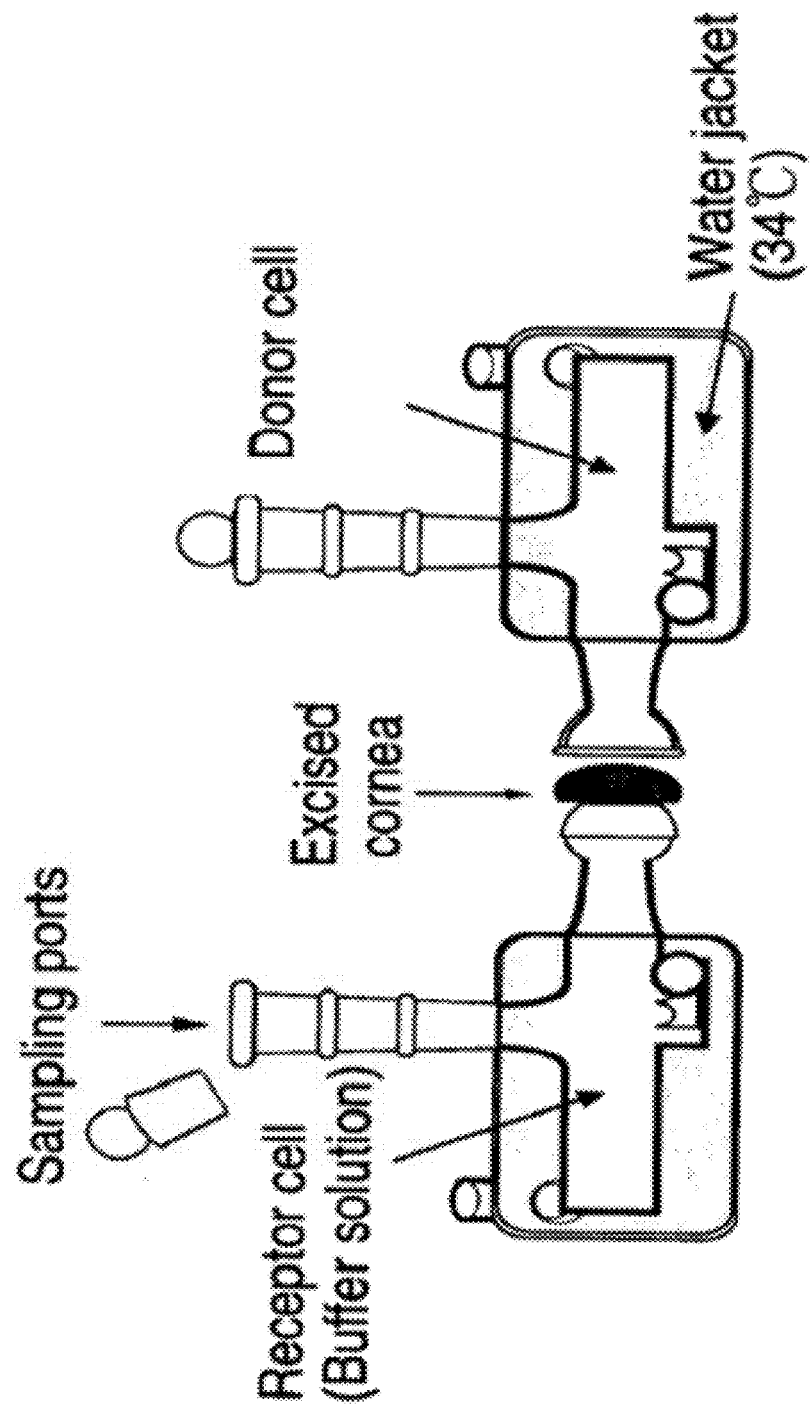
FIG. 9 shows the schematic of a standard side by side diffusion cell.

Three male rabbits (New Zealand) weighing 3-4 pounds. The age of the rabbits was 11-12 weeks. Immediately after sacrifice by an overdose of carbon dioxide gas, the eyes were enucleated, saline washed, and the corneas were separated for the use in permeation experiments. Each cornea was rinsed with freshly prepared receptor solution (Table 4) to remove excess stain. The six intact and fresh corneas were fixed between clamped donor and receptor compartments of an all glass side-by-side diffusion cell in such a way that its epithelial surface faces the donor compartment. FIG. 9 shows the schematic of a simple diffusion cell used in this experiment.

The corneal area available for permeation was 0.211 cm². The receptor compartment was filled with freshly prepared receptor solution at pH 7.2, as per the composition described in Table 4. An aliquot (5 mL) of sample #1 was placed on the two intact corneas, and the opening of the donor cells was sealed with a glass cover slip. After 10 minutes of applying sample #1, an aliquot (5 mL) of sample #2 was applied on the next two intact corneas. Again, after 10 minutes, sample #3 aliquot (5 mL) was applied on the remaining two intact corneas. The receptor fluid (5 mL in each receptor cell) was kept at constant temperature of 34° C. using constant stirring through water jacket in all the six cases. At predetermined time intervals of 10, 20, 40, 60, 80, 100, 120, 140, 160, and 180 minutes, 200 μL samples were withdrawn from the receptor solution. Thereafter, the same amount of the phosphate buffer solution was added to the receptor cell. The drug concentrations were assayed by UPLC.

3. Analysis
The dorzolamide and timolol maleate detection conditions were a gradient 1% Triethylamine (TEA) in water: acetonitrile method, performed at room temperature, with the flow rate of 0.7 mL/min, at 254 nm and 298 nm wavelength and 1 μL injection volume, on BEH C18 1.7 μm, 2.1×50 mm column.

4. Corneal Permeation Parameters Calculation
At the end of the experiment, each cornea (free from adhering sclera) was weighed after soaking in de-ionized water. The wet cornea was dried overnight in oven, and reweighed. From the difference of weights, corneal hydration was calculated. The final results of drug permeation were expressed as cumulative amount permeated (Q). The parameters that were calculated are as follows:

$$\text{Cumulative amount permeated } (Q, \text{ng/cm}^2)(t_i) = \frac{\text{Conc.}(t_i) \times \text{Cell volume (mL)} + \text{Conc.}(t_{i-1}) \times 0.2(\text{sampling volume(mL)})}{\text{Effective area(cm}^2)}$$

| | |
|---|---|
| | i = sampling number (1-10), Conc $(t_0) = 0$ |
| dQ/dt [μg/cm²/min] | Slope of cumulative amount curve |
| $t_d$ [min] | Intercept on the time axis |
| Permeability coefficient (P) [cm/sec] | $\dfrac{dQ}{dt} \times \dfrac{1}{C_d}$ |
| Diffusion coefficient (D) [cm²/sec] | $\dfrac{h^2}{6 \times t_d \times 60}$ |
| Partition Coefficient (K) [-] | $\dfrac{dQ}{dt} \times \dfrac{h}{D \times C_d} \times \dfrac{1}{60}$ |
| h [cm] | Thickness of cornea: 0.04 [cm] |
| $C_d$ [ng/mL] | Initial active ingredient (dorzolamide or timolol in donor solution) concentration μg/mL. |

Results and Discussion

The initial concentrations of dorzolamide and timolol determined by UPLC are given in Table 5.

TABLE 5

Initial concentration of test formulations

| Samples | Dorzolamide (mg/mL) | Timolol (mg/mL) |
|---|---|---|
| Test 1 | 23.023 | 4.7 |
| Test 2 | 21.48 | 4.51 |
| Test 3 | 22.208 | 4.72 |

The corneal hydration was measured based on the net wet weight and dry weight of cornea. Typically, the % hydrations for cornea in normal mammalian are in the range of 75-80%. Overall, there was no significant change in the % hydrations for all the test samples, and they were within the desired range in all the cases. Thus, the HP or polysorbate 80 did not have impact on corneal hydration.

TABLE 6

Percentage corneal hydration calculation.

| Sample | Final net wet weight (g) | Final net dry weight (g) | % corneal hydration |
|---|---|---|---|
| Test 1 | 0.0107 | 0.0017 | 84.11 |
| Test 1 | 0.0112 | 0.0019 | 83.06 |
| Test 2 | 0.0123 | 0.0023 | 80.16 |
| Test 2 | 0.0133 | 0.0023 | 82.70 |
| Test 3 | 0.0150 | 0.0024 | 84.00 |
| Test 3 | 0.0053 | 0.0012 | 77.40 |

Figure 10:
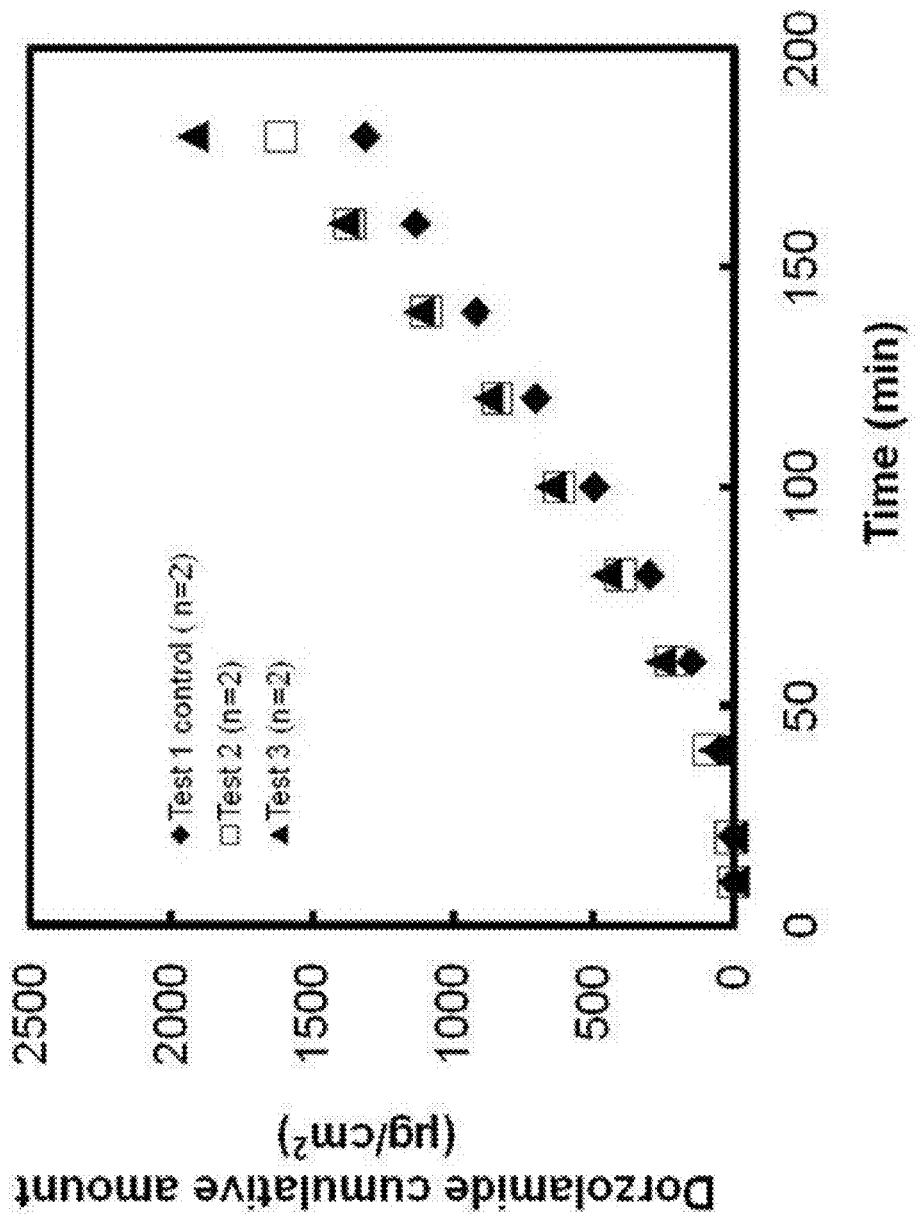
FIG. 10 shows the mean permeation profiles of dorzolamide (n=2) number of intact rabbit corneas tested.
Figure 11:
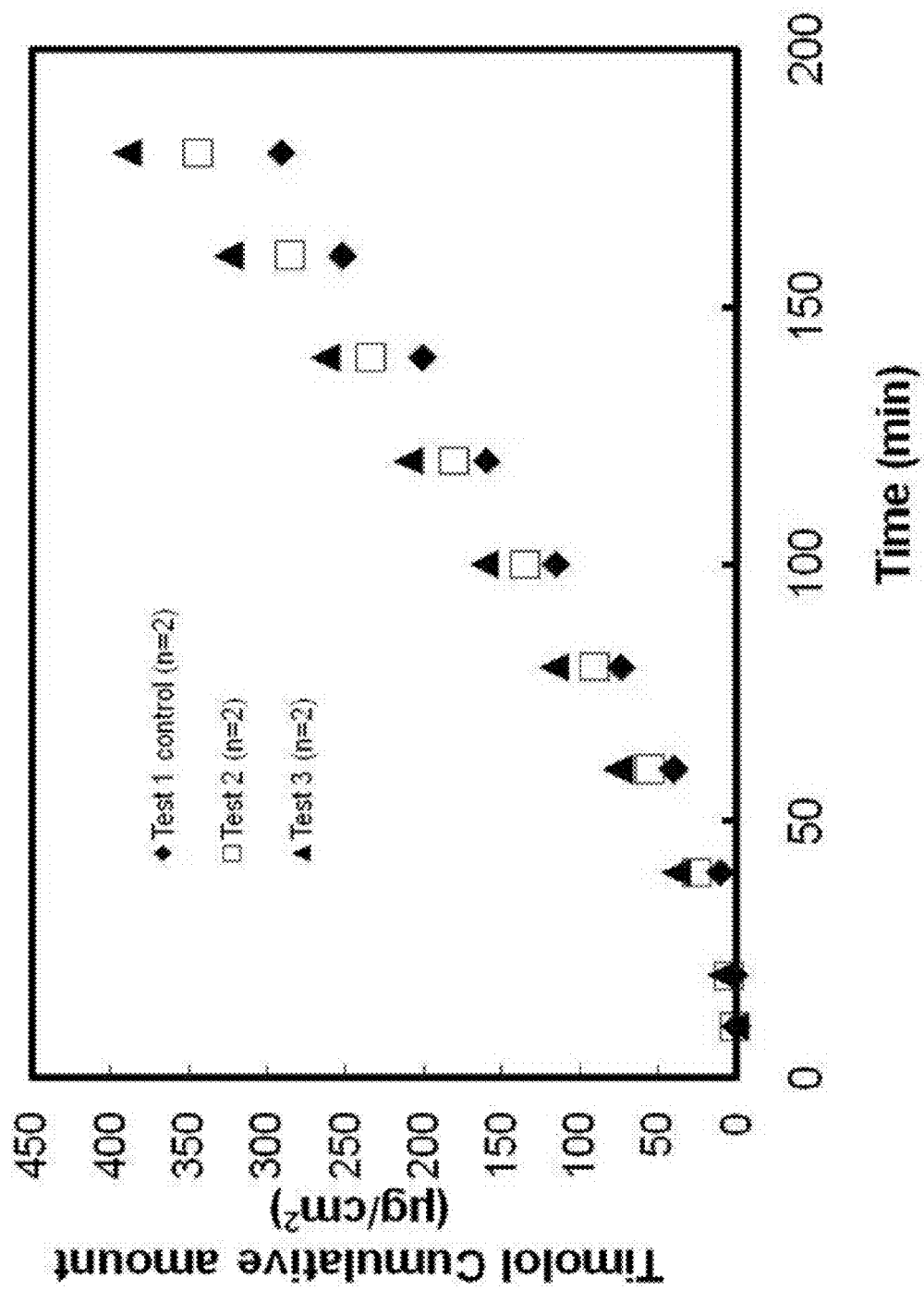
FIG. 11 shows the mean permeation profiles (n=2) of timolol through intact rabbit cornea.

FIGS. 10 and 11 reveal the corneal permeation profiles of dorzolamide and timolol, respectively. The time dependent permeation of dorzolamide and timolol was carefully examined across the isolated rabbit cornea at 34° C. The dorzolamide cumulative total amount permeated through the cornea, and the total amount permeated after 3 hours was relatively higher for the test formulation containing 0.5% HP compared to the control sample with no additives. Furthermore, the addition of polysorbate 80 along with HP enhanced the corneal permeation with more amount of dorzolamide permeated than the formulation containing only HP. Overall, the addition of 0.5% HP and 1% polysorbate 80 enhanced the corneal permeation rate of dorzolamide and timolol by about 25-30%. A similar trend was also observed for timolol (FIG. 11). Thus, the combination of HP and polysorbate 80 improved the corneal penetration of active ingredients.

Figure 12:
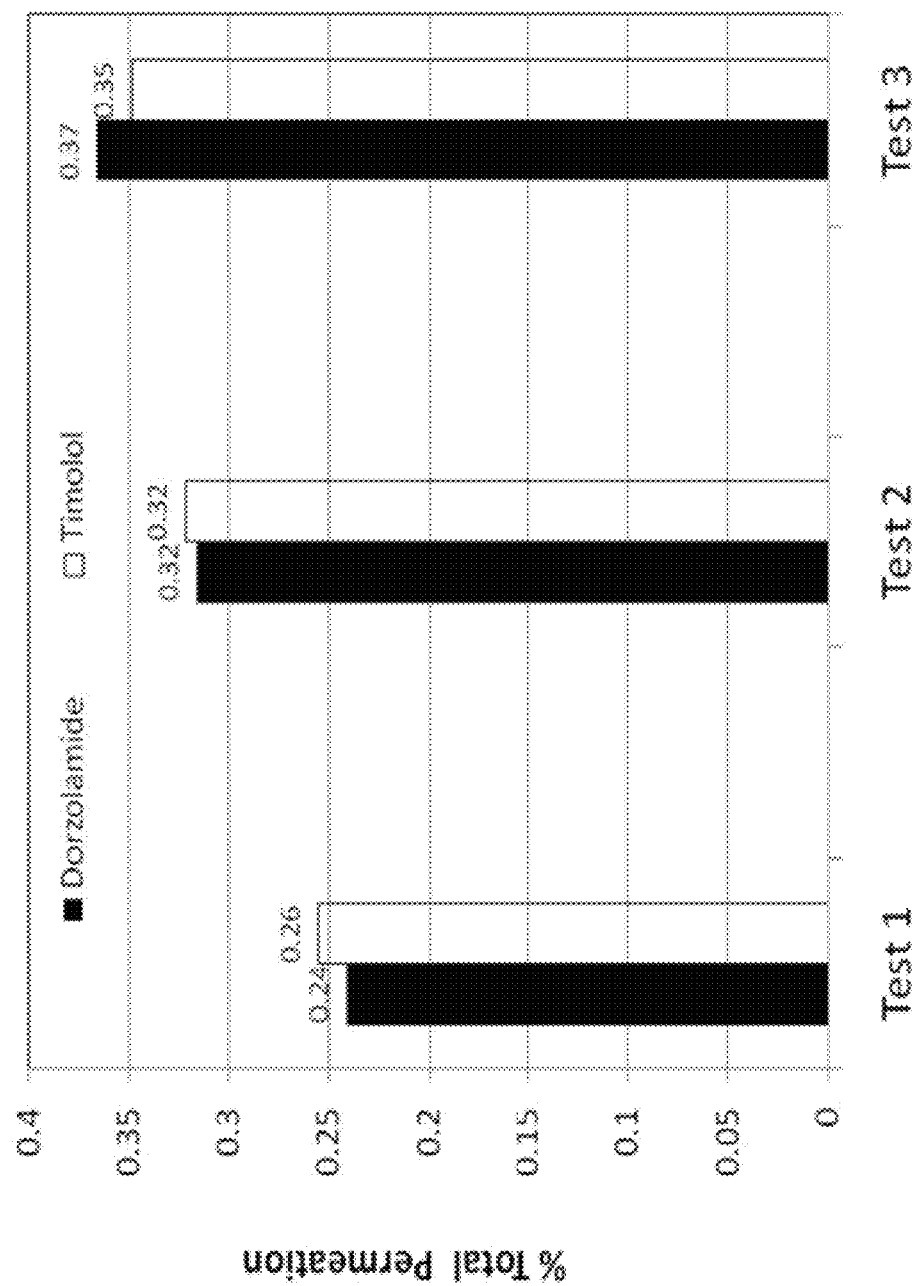
FIG. 12 shows the mean percentage total corneal permeation of dorzolamide and timolol after 180 minutes.

FIG. 12 shows the percentage total permeation of dorzolamide and timolol. Clearly, the presence of HP and polysorbate 80 increased the percentage of active ingredients (dorzolamide and timolol) permeated through the cornea. It should be noted that all test formulations had similar initial concentrations in case of dorzolamide and timolol (less than 10% change). Thus, it was easy to determine the influence of each additive under similar pH conditions. In comparing test 2 with test 1, the significance of using HP as an additive is clearly demonstrated.

Figure 13:
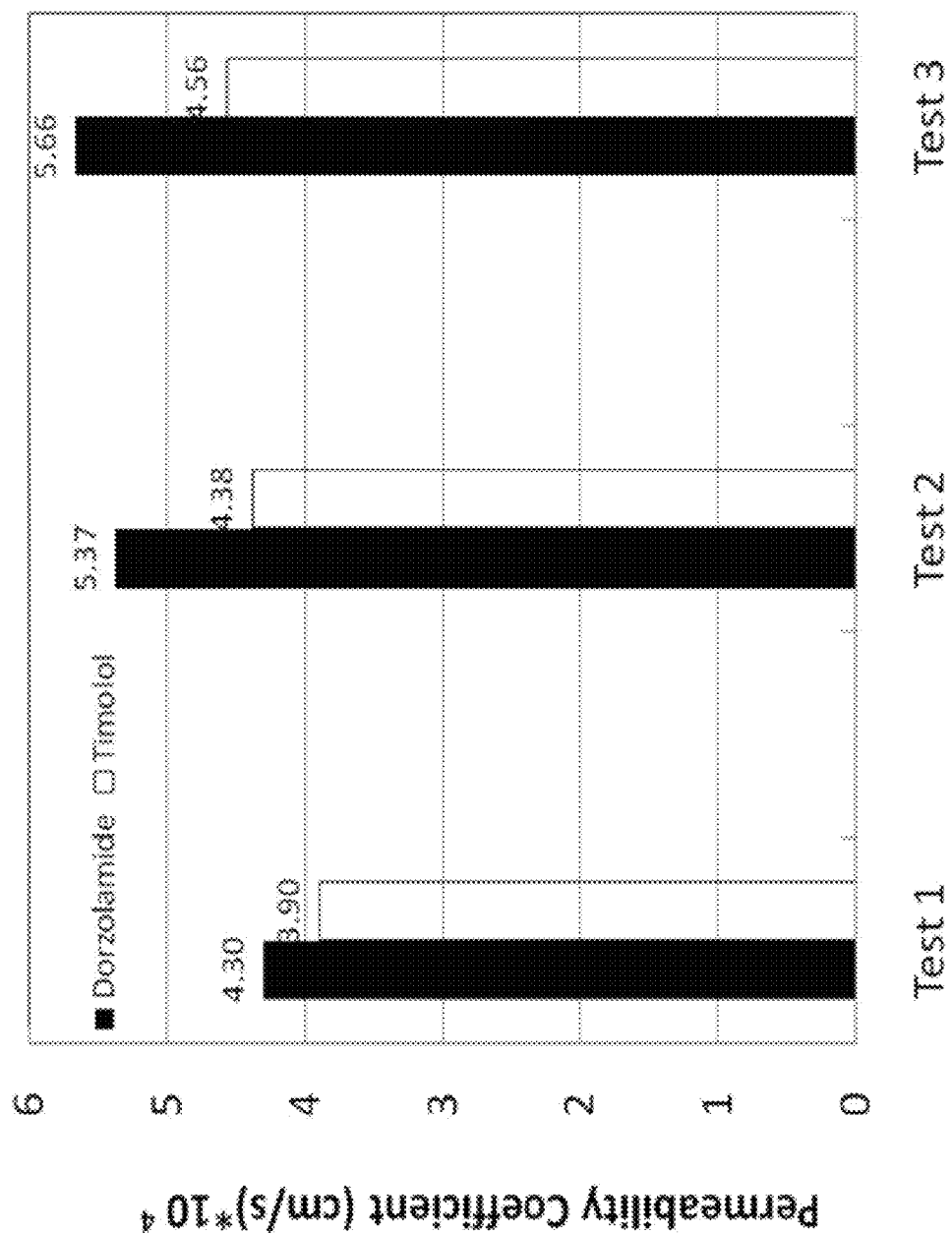
FIG. 13 shows the mean corneal permeability coefficients of dorzolamide and timolol.

FIG. 13 shows the corneal permeability coefficients of dorzolamide and timolol. The permeability coefficient was inversely proportional to the initial concentration of the drug in the donor solution. In the case of dorzolamide, the permeability coefficients for test 2 and test 3 were higher, suggesting that dorzolamide in the presence of 0.5% HP has enhanced corneal permeability rate compared to pH 5.65 control formulation (Test 1) containing no HP. Test 3 had relatively higher corneal permeability than Test 2, thereby indicating the influence of polysorbate 80. The polysorbate 80 may possibly act as a viscosity enhancer, thereby increasing the bioavailability of dorzolamide and timolol for corneal permeation. Overall, the data from FIG. 13 clearly indicates that the permeability coefficients of timolol and dorzolamide were higher for formulation tests 2 and 3 containing HP, and HP & polysorbate 80, respectively, in comparison to the control test 1 without HP at pH 5.65 (similar to COSOPT® active ingredient formulation).

Figure 14:
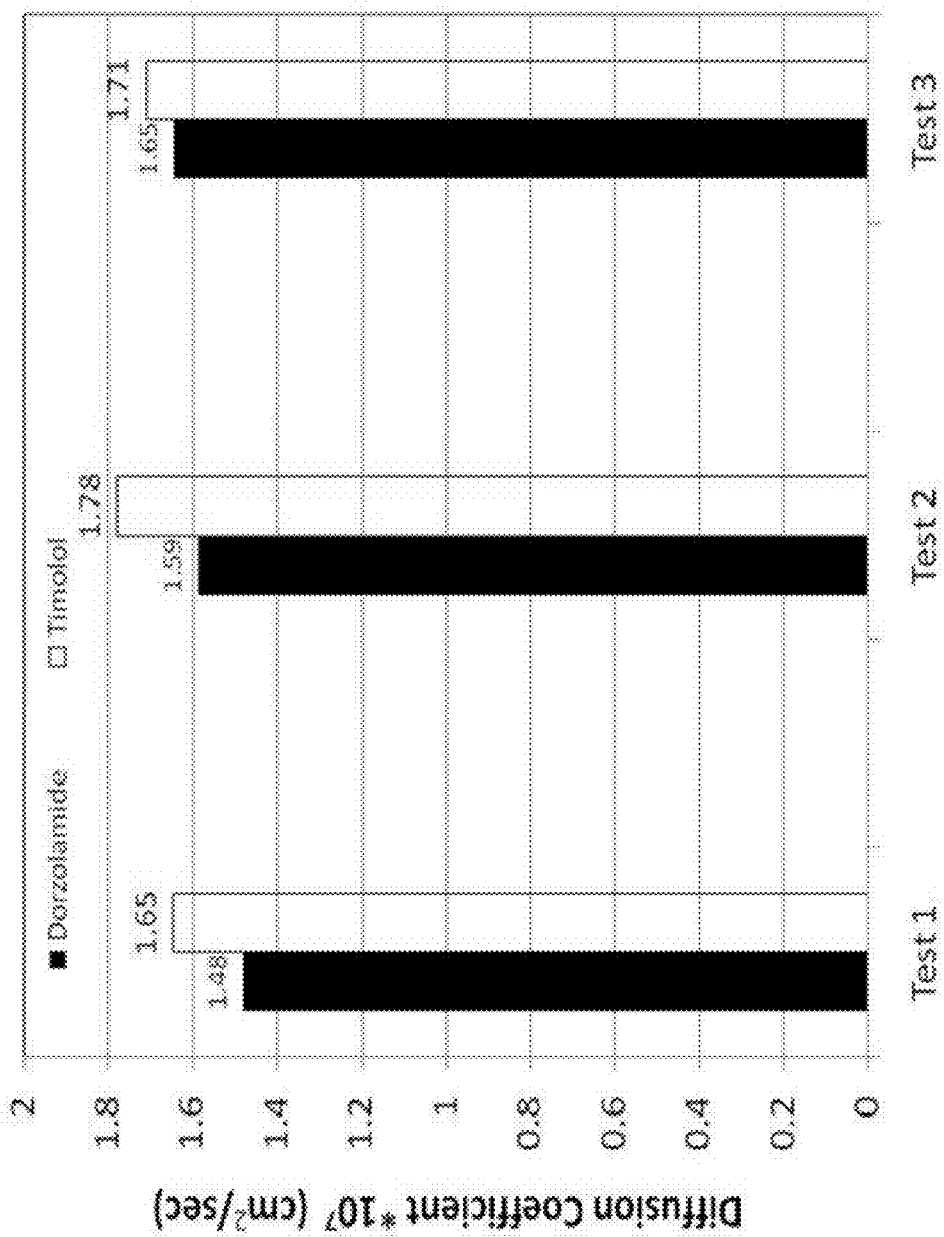
FIG. 14 shows the mean diffusion coefficients of dorzolamide and timolol for permeation through intact rabbit cornea.

The diffusion coefficient of dorzolamide and timolol, which is inversely proportional to the lag time, did not change significantly by the addition of HP and polysorbate 80 (see FIG. 14). Thus, HP and polysorbate 80 do not have any impact on the corneal surface. If the diffusion coefficient would have increased or decreased significantly, it would indicate the change in corneal surface properties. Since the diffusion coefficient is the inherent property of drug compound, it should not change with the addition of additives.

Figure 15:
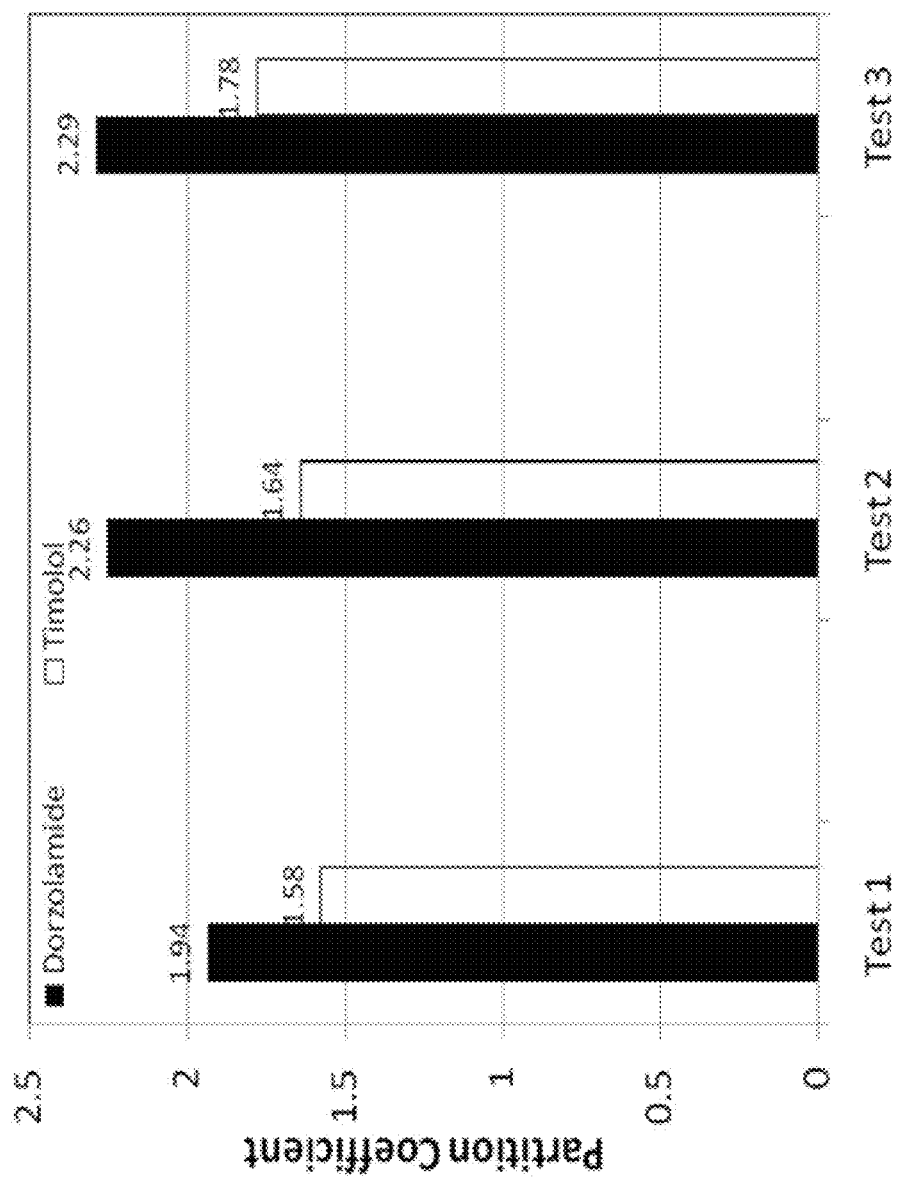
FIG. 15 shows the mean partition coefficients of dorzolamide and timolol for permeation through intact rabbit cornea.

HP promotes encapsulation of timolol and dorzolamide, and thus enhances the partitioning of timolol into corneal epithelium. This theory is also supported by the data in FIG. 15. The timolol and dorzolamide partition coefficient to the corneal surface for Test 3 is higher than Test 1, indicating the improvement in partitioning of timolol and dorzolamide into lypophilic corneal membrane in presence of 0.5% (w/v) highly functional HP. Thus, the improved permeation in the presence of HP is mainly because of improved portioning to the epithelium. The partitioning could be further enhanced by increasing the concentration of HP in the formulation solution. HP enhances corneal permeation mainly because a) molecular encapsulation within the branched structures of highly functional polyethyleneimine, b) electrostatic interactions between the drug molecules and ionic functional amine groups of HP, and c) the muco-adhesive behavior of charged HP.

The addition of 0.5% HP and 1% polysorbate 80 enhanced the corneal permeation rate of dorzolamide and timolol by about 25-30%. The presence of hyperbranched polymer (HP) increased the partitioning of dorzolamide and timolol at pH 5.65 into the corneal membrane. There was insignificant change in the corneal diffusion rate and corneal hydration rate by the addition of HP and polysorbate 80, suggesting that these additives did not have a harmful impact on the cornea surface. The corneal permeability coefficients of dorzolamide and timolol were relatively higher in the presence of HP, suggesting the significance of HP as an effective drug carrier additive. Thus, the present inventors discovered a novel formulation with enhanced corneal permeation compared to the current market product. The corneal permeation could be further enhanced by increasing the concentration of HP.

Conclusion

The cumulative amount permeated of dorzolamide and timolol at pH 5.65 in the presence of additives such as HP was relatively high, compared to the control formulation with no additives (COSOPT® active ingredients formulation). The 0.5% (w/v) HP and 1% (w/v) polysorbate 80 addition to the formulation enhanced the corneal permeation rate of dorzolamide and timolol by about 25-30%. The enhancement of corneal permeation is promoted by the molecular encapsulation of active ingredients into the branched pockets of HP and electrostatic interactions between cationic HP and negatively charged corneal surface at pH 5.65. The partitioning of active ingredients into the corneal epithelium increases in presence of HP. Thus, the combination of HP and polysorbate 80 could be very effective for increasing the ocular bioavailability of COSOPT® active ingredients.

EXPERIMENTAL EXAMPLE 5

Solubility enhancement of brinzolamide in aqueous solution containing hyperbranched polymer (HP) or a combination of hyperbranched polymer and polysorbate 80, or polyethylene glycol and polysorbate 80 combinations at pH 7 in phosphate buffer.

The aqueous solubility of brinzolamide in the presence of timolol at pH 7 in 10 mM phosphate buffer was studied.

TABLE 7

Different Test formulations prepared in phosphate buffer at pH 7.
Methods

| Content | Control Sample | S #1 | S #2 | S #3 | S #4 | S #5 | S #6 | S #7 | S #8 |
|---|---|---|---|---|---|---|---|---|---|
| Brinzolamide | 1 | >1 | >1 | >1 | >1 | >1 | >1 | >1 | >1 |
| Lupasol ® PS (MW = 750k) | — | 0.5 | 1 | 2 | 0.5 | 1 | 2 | — | — |
| PEG 400 | — | — | — | — | — | — | — | 2 | — |
| PEG 8000 | — | — | — | — | — | — | — | — | 2 |
| Polysorbate 80 | — | — | — | — | 1 | 1 | 1 | 1 | 1 |
| In 10 mM citrate or phosphate buffer (add 1M NaOH) | Adjust pH to 7 | Adjust pH to 7 | Adjust pH to 7 | Adjust pH to 7 | Adjust pH to 7 | Adjust pH to 7 | Adjust pH to 7 | Adjust pH to 7 | Adjust pH to 7 |

A suspension of brinzolamide in phosphate buffer containing 1% was prepared for the control sample. Similar suspensions containing excess of brinzolamide (>1%) were also prepared in aqueous solution (10 mM phosphate buffer) containing different combinations of hyperbranched polymer (Lupasol® PS), PEG and polysorbate 80 as per Table 7 above. The final pH was adjusted to 7 with 1 M NaOH. The suspension solutions were first stirred for 10 min at room temperature (with heating up to 60° C. for 5 minutes). After allowing the suspensions to equilibrate at room temperature for additional 30 minutes, the suspension solutions were then sonicated for 10 min and finally filtered through 0.45 μm syringe filters. The filtrates were analyzed for brinzolamide concentration using UPLC after diluting each sample with ultrapure water (dilution factor=1000). The brinzolamide detection was performed at the following conditions: a gradient 1% Triethylamine (TEA) III water:acetonitrile method, performed at room temperature, with the flow rate of 0.7 mL/min, at 254 nm wavelength and 1 1 μL injection volume, on BEH C18 1.7 μm, 2.1×50 mm column. A calibration curve was prepared to find the brinzolamide concentration.

Results and Discussion

Figure 16:
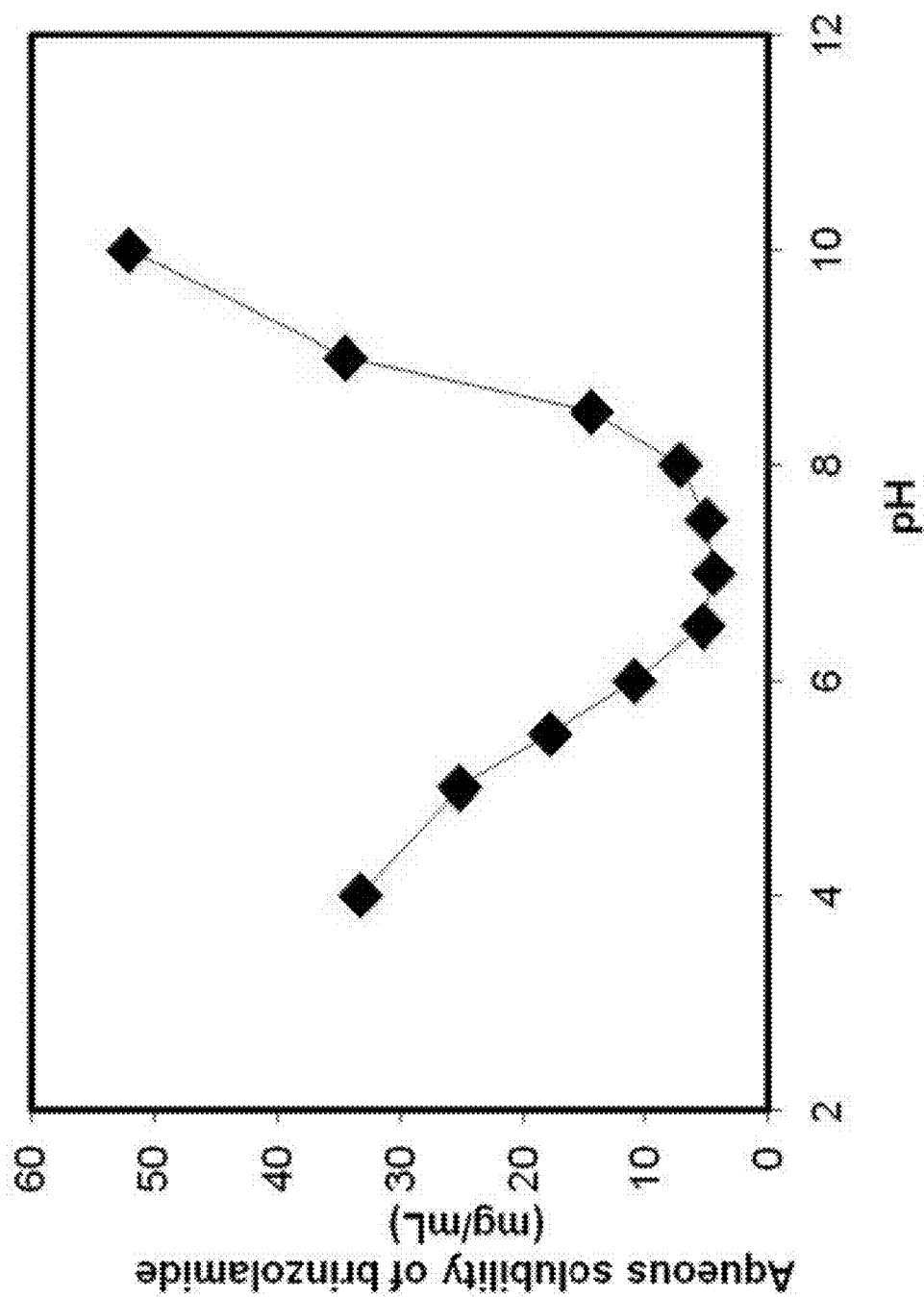
FIG. 16 shows the aqueous solubility of brinzolamide in 10 mM phosphate buffer at different pH.

FIG. 16 shows the brinzolamide solubility in 10 mM phosphate buffer at different pH values. It is clear that the aqueous solubility of brinzolamide decreases as the pH increases from 4 towards 7. The solubility of brinzolamide is least at pH 7, consistent with the complete non-ionic behavior at pH 7. As % ionization of brinzolamide increases with the increase in pH from 8.4 towards 10, the solubility increases steeply consistent with the anionic nature of brinzolamide in that pH range. The solubility properties are very similar to dorzolamide. Therefore, it is important to develop a lypophilic brinzolamide drug with enhanced solubility close to pH 7.4 (pH of tear fluid is 7.44) in order to enhance ocular bioavailability and to decrease eye irritation appearance of brinzolamide.

Figure 17:
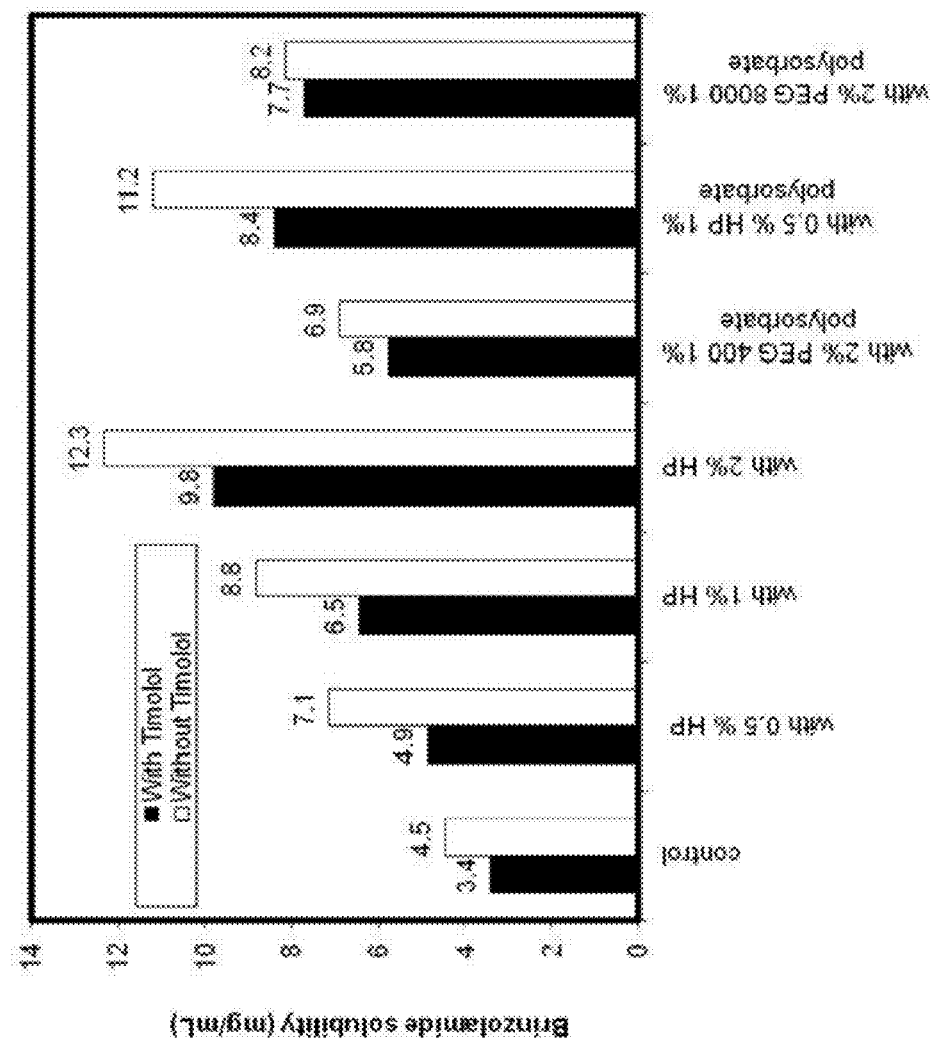
FIG. 17 shows the maximum aqueous solubility of brinzolamide at pH 7 with addition of additives in the absence and presence of 0.5% timolol in the aqueous solution in all cases.

In this study, the present inventors used hyperbranched polymers, PEG, and polysorbate 80 as solubility enhancer additives. Different combinations were attempted at pH 7. In FIG. 17, the solubility of brinzolamide is shown to increase with the addition of additives.

As shown in FIG. 17, the solubility of brinzolamide increases with the increase in the concentration of HP in both the cases (with and without timolol). The solubility of brinzolamide in absence of timolol with 0.5% HP and 1% polysorbate 80 is about 11 mg/mL. The addition of PEG 8000 over PEG 400 seems to enhance the solubility of brinzolamide. However, the solubility for control solution as well as all the formulations with additives containing 0.5% timolol was relatively lower. Thus, timolol, which is relatively more soluble in water than brinzolamide at pH 7, makes an impact on aqueous solubility of brinzolamide by its presence in the topical formulation sample. These results are very similar to the results (discussed above) regarding another carbonic anhydrase called dorzolamide. The decrease in solubility by highly soluble ionic timolol at pH 7 could be due to change in ionic strength of the solution by addition of timolol or salting out effect. While the market Azarga® product has brinzolamide 10 mg/mL+timolol 5 mg/mL ophthalmic suspension at pH 7.4, the enhancement of solubility at pH 7 by addition of HP or PEG will have useful contribution to efficacy enhancement of drug by increasing the dosage to greater than 1%.

The addition of polysorbate 80 to HP increases the brinzolamide solubility by preventing the precipitation of ionic pair of HP and brinzolamide. Polysorbate 80 may act as a surfactant thereby reducing the aggregation of brinzolamide after phase separation in presence of HP. A combination of 0.5% HP and 1% polysorbate could be very effective in the presence of 0.5% timolol formulation at pH 7.

The improvement in aqueous solubility of brinzolamide in presence of timolol was significant with the additions of hyperbranched polymer or a combination of PEG and polysorbate 80 at pH 7. The polysorbate 80 helps in dispersing the brinzolamide molecules and inhibits the precipitation in water in presence of PEG. A combination of HP and polysorbate 80 could be the best combination for enhancement of brinzolamide solubility in presence of timolol at pH 7. From the results, it can be concluded that hyperbranched polymer and polysorbate 80 significantly enhance the solubility of hydrophobic brinzolamide in presence of Timolol at pH 7. Hydrophilic polyethylene glycol also turned out to be a brinzolamide solubility enhancer. Furthermore, a combination of low concentrations of polysorbate 80 and PEG 8000 also proved to be a very useful additive for enhancement of solubility of hydrophobic brinzolamide. Overall, a formulation at pH 7 with optimized concentration of hyperbranched polymer (Lupasol® PS) and polysorbate 80 could be very useful for increasing the ocular bioavailability. Conclusion The results clearly indicate the advantages of using hyperbranched polymers and polysorbate 80 as hydrophobic brinzolamide solubility enhancing additives at pH values closer to physiological pH that are more conducive for penetration of close to 1% (w/v) brinzolamide through cornea membrane. In addition, these polymers may provide bioadhesive properties necessary for increasing the ocular residence time of brinzolamide on eye surface. Polysorbate 80 also proved to be an effective emulsifier suppressing the precipitation of poorly soluble brinzolamide at pH 7 in presence of HP. Timolol may have an effect on the solubility of brinzolamide by changing the ionic strength of the solution.

Industrial Applicability

According to the present invention, an ophthalmic composition comprising a hyperbranched polymer, which shows increased aqueous solubility of carbonic anhydrase inhibitors, such as dorzolamide or brinzolamide, can be provided. The ophthalmic composition may also comprise a non-ionic surfactant and/or a beta-blocker. The ophthalmic compositions of the present invention result in increased permeation of the active agent into the cornea. Therefore, the overall ocular bioavailability and hence the therapeutic activity of the topical ophthalmic solution containing a carbonic anhydrase inhibitor and beta blocker (active ingredients) can be increased compared to current relevant ophthalmic market products available. The topical ophthalmic compositions presented in this invention provide more potent anti-glaucoma compositions that may increase patient compliance by increasing ocular bioavailability.

While some of the embodiments of the present invention have been described in detail in the above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

The invention claimed is:

1. An ophthalmic composition comprising a hyperbranched polymer and a carbonic anhydrase inhibitor, wherein:
   the hyperbranched polymer is polyethyleneimine,
   the hyperbranched polymer is a solubility enhancer for improving therapeutic activity of the carbonic anhydrase inhibitor, and
   the hyperbranched polymer is a cornea permeation enhancer of the carbonic anhydrase inhibitor.

2. The ophthalmic composition according to claim 1, further comprising a non-ionic surfactant.

3. The ophthalmic composition according to claim 1, wherein the molecular weight of the hyperbranched polymer is from 1,000 to 750,000 Daltons ($M_w$).

4. The ophthalmic composition according to claim 1, wherein the pH range is 5.0 to 8.0.

5. The ophthalmic composition according to claim 1, wherein the concentration of the hyperbranched polymer is 0.001% to 5%.

6. The ophthalmic composition according to claim 1, further comprising a beta-blocker.

7. The ophthalmic composition according to claim 1, wherein the carbonic anhydrase inhibitor is selected from the group consisting of dorzolamide, brinzolamide and acetazolamide.

8. The ophthalmic composition according to claim 2, wherein the non-ionic surfactant is selected from the group consisting of polysorbate 80, hydroxypropyl methylcellulose, and hydroxyethyl cellulose.

9. The ophthalmic composition according to claim 6, wherein the beta-blocker is selected from the group consisting of carteolol, levobunolol, betaxolol, metipranolol, timolol and propranolol.

10. An ophthalmic composition comprising a hyperbranched polymer, timolol, dorzolamide and polysorbate 80, wherein the hyperbranched polymer is polyethyleneimine.

11. An ophthalmic composition comprising a hyperbranched polymer, timolol, brinzolamide and polysorbate 80, wherein the hyperbranched polymer is polyethyleneimine.

* * * * *